(12) United States Patent
Harlev et al.

(10) Patent No.: US 9,131,869 B2
(45) Date of Patent: Sep. 15, 2015

(54) TRACKING USING FIELD MAPPING

(75) Inventors: Doron Harlev, Cambridge, MA (US);
Derek Kane, Manchester, NH (US);
Brian Stewart, North Reading, MA (US); Paul Hultz, Brookline, NH (US);
Alpar Csendes, Burlington, MA (US)

(73) Assignee: Rhythmia Medical, Inc., Burlington, MA (US)

( * ) Notice: Subject to any disclaimer, the term of this patent is extended or adjusted under 35 U.S.C. 154(b) by 539 days.

(21) Appl. No.: 12/777,397

(22) Filed: May 11, 2010

(65) Prior Publication Data
US 2011/0282186 A1    Nov. 17, 2011

(51) Int. Cl.
| A61B 5/053 | (2006.01) |
| A61B 5/05 | (2006.01) |
| A61B 5/06 | (2006.01) |
| A61B 5/00 | (2006.01) |
| A61B 5/042 | (2006.01) |

(52) U.S. Cl.
CPC ............ *A61B 5/0538* (2013.01); *A61B 5/05* (2013.01); *A61B 5/053* (2013.01); *A61B 5/0536* (2013.01); *A61B 5/061* (2013.01); *A61B 5/063* (2013.01); *A61B 5/0044* (2013.01); *A61B 5/0422* (2013.01); *A61B 5/065* (2013.01); *A61B 5/068* (2013.01); *A61B 5/6846* (2013.01); *A61B 5/6858* (2013.01); *A61B 5/6869* (2013.01)

(58) Field of Classification Search
USPC ......... 600/407, 424, 425, 427, 481, 508, 509, 600/513
See application file for complete search history.

(56) References Cited

U.S. PATENT DOCUMENTS

| 4,649,924 A | 3/1987 | Taccardi |
| 4,674,518 A | 6/1987 | Salo ............................. 128/695 |
| 4,840,182 A | 6/1989 | Carlson ......................... 128/694 |
| 4,890,623 A | 1/1990 | Cook et al. |
| 4,920,490 A | 4/1990 | Isaacson .................. 364/413.13 |
| 4,940,064 A | 7/1990 | Desai et al. |
| 5,156,151 A | 10/1992 | Imran |
| 5,228,442 A | 7/1993 | Imran |
| 5,279,299 A | 1/1994 | Imran |
| 5,284,142 A | 2/1994 | Goble et al. ............... 128/653.1 |
| 5,297,549 A | 3/1994 | Beatty et al. |
| 5,300,068 A | 4/1994 | Rosar et al. ..................... 606/34 |
| 5,311,866 A | 5/1994 | Kagan et al. |
| 5,313,943 A | 5/1994 | Houser et al. |
| 5,341,807 A | 8/1994 | Nardella |
| 5,345,936 A | 9/1994 | Pomeranz et al. |
| 5,381,333 A | 1/1995 | Isaacson et al. ......... 364/413.13 |
| 5,415,166 A | 5/1995 | Imran |
| 5,425,364 A | 6/1995 | Imran |
| 5,456,254 A | 10/1995 | Imran |
| 5,471,982 A | 12/1995 | Edwards et al. |
| 5,480,422 A | 1/1996 | Ben-Haim |
| 5,500,011 A | 3/1996 | Desai |

(Continued)

OTHER PUBLICATIONS

Authorized officer Blaine R. Copenheaver, International Search Report and Written Opinion in PCT/US2011/032399 mailed Jul. 8, 2011, 13 pages.

(Continued)

*Primary Examiner* — Long V Le
*Assistant Examiner* — Michael Kellogg
(74) *Attorney, Agent, or Firm* — Faegre Baker Daniels LLP

(57) ABSTRACT

Methods and systems for determining the position of an object, such as tracking the position of one or more catheters in a patient's heart cavity are disclosed herein.

40 Claims, 12 Drawing Sheets

(56) References Cited

U.S. PATENT DOCUMENTS

| | | | |
|---|---|---|---|
| 5,553,611 A | 9/1996 | Budd et al. | 128/642 |
| 5,568,384 A * | 10/1996 | Robb et al. | 715/202 |
| 5,568,809 A | 10/1996 | Ben-Haim | |
| 5,577,502 A | 11/1996 | Darrow et al. | 128/653.1 |
| 5,588,429 A | 12/1996 | Isaacson et al. | |
| 5,647,870 A | 7/1997 | Kordis et al. | |
| 5,662,108 A | 9/1997 | Budd et al. | |
| 5,681,280 A | 10/1997 | Rusk et al. | |
| 5,681,308 A | 10/1997 | Edwards | |
| 5,687,737 A | 11/1997 | Branham et al. | |
| 5,697,377 A | 12/1997 | Wittkampf | |
| 5,699,796 A | 12/1997 | Littmann et al. | |
| 5,704,365 A | 1/1998 | Albrecht et al. | |
| 5,722,402 A | 3/1998 | Swanson et al. | 128/642 |
| 5,846,198 A | 12/1998 | Killmann | 600/424 |
| 5,848,972 A | 12/1998 | Triedman et al. | |
| 5,871,443 A | 2/1999 | Edwards et al. | |
| 5,921,982 A | 7/1999 | Lesh et al. | 606/41 |
| 5,971,933 A | 10/1999 | Gopakumaran et al. | 600/526 |
| 5,983,126 A | 11/1999 | Wittkampf | |
| 6,050,267 A | 4/2000 | Nardella et al. | |
| 6,064,905 A | 5/2000 | Webster | |
| 6,095,150 A | 8/2000 | Panescu et al. | 128/899 |
| 6,167,296 A | 12/2000 | Shahidi | |
| 6,236,886 B1 | 5/2001 | Cherepenin et al. | |
| 6,240,307 B1 | 5/2001 | Beatty et al. | |
| 6,246,898 B1 | 6/2001 | Vesely et al. | |
| 6,254,536 B1 | 7/2001 | DeVito | 600/300 |
| 6,278,894 B1 | 8/2001 | Salo et al. | 600/547 |
| 6,298,257 B1 | 10/2001 | Hall et al. | 600/407 |
| 6,308,093 B1 | 10/2001 | Armoundas et al. | 600/509 |
| 6,314,310 B1 | 11/2001 | Ben-Haim et al. | |
| 6,317,619 B1 | 11/2001 | Boernert et al. | 600/410 |
| 6,318,375 B1 | 11/2001 | Plicchi et al. | 128/899 |
| 6,360,123 B1 | 3/2002 | Kimichi et al. | 600/547 |
| 6,368,285 B1 | 4/2002 | Osadchy et al. | 600/508 |
| 6,400,981 B1 | 6/2002 | Govari | |
| 6,516,807 B1 | 2/2003 | Panescu et al. | |
| 6,547,082 B1 | 4/2003 | Babini | 211/41.17 |
| 6,556,695 B1 | 4/2003 | Packer et al. | |
| 6,574,492 B1 | 6/2003 | Ben-Haim et al. | |
| 6,574,498 B1 | 6/2003 | Gilboa | 600/424 |
| 6,593,884 B1 | 7/2003 | Gilboa et al. | |
| 6,600,948 B2 | 7/2003 | Ben-Haim et al. | |
| 6,603,996 B1 | 8/2003 | Beatty et al. | |
| 6,631,290 B1 | 10/2003 | Guck et al. | |
| 6,640,119 B1 | 10/2003 | Budd et al. | 600/374 |
| 6,650,927 B1 | 11/2003 | Keidar | |
| 6,690,963 B2 | 2/2004 | Ben-Haim et al. | |
| 6,701,176 B1 | 3/2004 | Halperin et al. | |
| 6,728,562 B1 | 4/2004 | Budd et al. | |
| 6,773,402 B2 | 8/2004 | Govari et al. | |
| 6,807,439 B2 | 10/2004 | Edwards et al. | 600/420 |
| 6,826,421 B1 | 11/2004 | Beatty et al. | |
| 6,837,886 B2 | 1/2005 | Collins et al. | |
| 6,839,588 B1 | 1/2005 | Rudy | |
| 6,847,839 B2 | 1/2005 | Ciaccio et al. | |
| 6,872,428 B2 | 3/2005 | Yang et al. | 427/568 |
| 6,892,090 B2 | 5/2005 | Verard et al. | 600/424 |
| 6,892,091 B1 | 5/2005 | Ben-Haim et al. | 600/509 |
| 6,939,309 B2 | 9/2005 | Beatty et al. | 600/508 |
| 6,978,168 B2 | 12/2005 | Beatty et al. | |
| 6,990,370 B1 | 1/2006 | Beatty et al. | 600/509 |
| 7,016,719 B2 | 3/2006 | Rudy et al. | |
| 7,198,635 B2 | 4/2007 | Danek et al. | |
| 7,263,397 B2 | 8/2007 | Hauck et al. | 600/374 |
| 7,289,843 B2 | 10/2007 | Beatty et al. | |
| 7,515,954 B2 | 4/2009 | Harlev et al. | |
| 7,930,018 B2 | 4/2011 | Harlev et al. | |
| 7,957,791 B2 | 6/2011 | Harlev et al. | |
| 8,942,786 B2 | 1/2015 | Harley et al. | |
| 2003/0018251 A1 | 1/2003 | Solomon | |
| 2003/0065271 A1 | 4/2003 | Khoury | |
| 2003/0076277 A1 | 4/2003 | Muramatsu et al. | 345/1.1 |
| 2003/0216630 A1 | 11/2003 | Jersey-Willuhn et al. | |
| 2004/0077942 A1 | 4/2004 | Hall et al. | 600/428 |
| 2004/0097806 A1 | 5/2004 | Hunter et al. | |
| 2004/0254437 A1 | 12/2004 | Hauck et al. | |
| 2005/0033136 A1 | 2/2005 | Govari et al. | |
| 2005/0033137 A1 | 2/2005 | Oral et al. | |
| 2005/0038337 A1 | 2/2005 | Edwards | 600/424 |
| 2005/0054918 A1 | 3/2005 | Sra | |
| 2005/0154282 A1 | 7/2005 | Li et al. | 600/407 |
| 2005/0288599 A1 | 12/2005 | MacAdam et al. | 600/509 |
| 2006/0085049 A1 | 4/2006 | Cory et al. | 607/48 |
| 2006/0116575 A1 | 6/2006 | Willis | |
| 2006/0122526 A1 | 6/2006 | Berenfeld et al. | |
| 2006/0173251 A1 | 8/2006 | Govari et al. | 600/306 |
| 2006/0241401 A1 | 10/2006 | Govari et al. | 600/424 |
| 2007/0016007 A1 | 1/2007 | Govari et al. | 600/424 |
| 2007/0038078 A1 | 2/2007 | Osadchy | 600/424 |
| 2007/0083194 A1 | 4/2007 | Kunis et al. | |
| 2007/0299351 A1 | 12/2007 | Harlev et al. | 600/509 |
| 2007/0299353 A1 * | 12/2007 | Harlev et al. | 600/509 |
| 2008/0058657 A1 | 3/2008 | Schwartz et al. | |
| 2008/0190438 A1 * | 8/2008 | Harlev et al. | 128/898 |
| 2008/0234588 A1 | 9/2008 | Feldman et al. | |
| 2009/0177072 A1 | 7/2009 | Harlev et al. | |
| 2009/0253976 A1 * | 10/2009 | Harlev et al. | 600/374 |
| 2009/0264746 A1 | 10/2009 | Markowitz et al. | |
| 2010/0106009 A1 * | 4/2010 | Harlev et al. | 600/424 |
| 2010/0106154 A1 | 4/2010 | Harlev et al. | |
| 2010/0286550 A1 * | 11/2010 | Harlev et al. | 600/547 |
| 2011/0282186 A1 | 11/2011 | Harlev et al. | |

OTHER PUBLICATIONS

U.S. Appl. No. 13/044,937, filed Mar. 10, 2011, Harlev et al.

Adams et al., "Seeded Region Growing," IEEE Transactions on Pattern Analysis and Machine Intelligence 16(6):641-647 (1994).

Supplementary European Search Report in Application No. 07798369.0 mailed Jul. 30, 2010, 6 pages.

Authorized officer Blaine R. Copenheaver, International Search Report and Written Opinion in PCT/US2009/036099 mailed Apr. 28, 2009, 21 pages.

Authorized officer Brian T. Gedeon, Notice of Allowance in U.S. Appl. No. 11/451,898 dated Jan. 29, 2009, 6 pages.

Authorized officer Brian T. Gedeon, Notice of Allowance in U.S. Appl. No. 12/138,678 dated Feb. 1, 2011, 7 pages.

Authorized officer Brian T. Gedeon, Office Action in U.S. Appl. No. 11/451,898 dated Sep. 25, 2008, 20 pages.

Authorized officer Carl H. Layno, International Search Report and Written Opinion in PCT/US07/070854 mailed Sep. 12, 2008, 15 pages.

Authorized officer Lee W. Young, International Search Report and Written Opinion in PCT/US08/52385 mailed Aug. 8, 2008, 8 pages.

Authorized officer Nora Linder, International Preliminary Report on Patentability in PCT/US2008/052385 mailed Aug. 20, 2009, 7 pages.

Baan et al., "Continuous Measurement of Left Ventricular Volume in Animals and Humans by Conductance Catheter," Circulation 70:812-823.

Ben-Haim et al., "Nonfluoroscopic, in Vivo Navigation and Mapping Technology," Nature Medicine 2(12):1393-1395 (1996).

Besl et al., "A Method for Registration of 3-D Shapes," IEEE Transactions on Pattern Analysis and Machine Intelligence 14(2):239-256 (1992).

Blomström-Lundqvist et al., "ACC/AHA/ESC Guidelines for the Management of Patients With Supraventricular Arrhythmias-Executive Summary," Journal of the American College of Cardiology 42(8):1493-1531 (2003).

Breithardt et al., "Standards for Analysis of Ventricular Late Potentials Using High-Resolution or Signal-Averaged Electrocardiography," AHA Medical/Scientific Statement—Special Report, Circulation 83(4):1481-1488 (1991).

Brooks et al., "Electrical Imaging of the Heart," IEEE Signal Processing Magazine pp. 24-42 (1997).

Caspi et al., "Regenerating the Heart Using Human Embryonic Stem Cells—from Cell to Bedside," IMAJ 8:208-214 (2006).

(56) References Cited

OTHER PUBLICATIONS

De Groot et al., "Three-Dimensional Catheter Positioning During Radiofrequency Ablation in Patients: First Application of a Real-Time Position Management System," Journal of Cardiovascular Electrophysiology 11:1183-1192 (2000).
Donahue et al., "Focal Modification of Electrical Conduction in the Heart by Viral Gene Transfer," Nature Medicine 6(12):1395-1398 (2000).
Dong et al., "Integrated Electroanatomic Mapping With Three-Dimensional Computed Tomographic Images for Real-Time Guided Ablations," Circulation 113:186-194 (2006).
Durrer et al., "Total Excitation of the Isolated Human Heart," Circulation XLI:899-912 (1970).
Ector et al., "Cardiac Three-Dimensional Magnetic Resonance Imaging and Fluoroscopy Merging," Circulation 112:3769-3776 (2005).
Fish & Richardson, Response to Office Action in U.S. Appl. No. 11/451,898, filed Nov. 4, 2008 (25 pages).
Friedman, "Catheter Cryoablation of Cardiac Arrhythmias," Current Opinion in Cardiology 20:48-54 (2005).
Friedman, "Novel Mapping Techniques for Cardiac Electrophysiology," Heart 87:575-582 (2002).
Geddes et al., "Criteria for the Selection of Materials for Implanted Electrodes," Annals of Biomedical Engineering 31:879-890 (2003).
Gepstein et al., "A Novel Method for Nonfluoroscopic Catheter-Based Electroanatomical Mapping of the Heart," Circulation 95:1611-1622 (1997).
Huang et al., "Development of a Third Generation Intraventricular Impedance Imaging (Iii) System Evaluation of Hardware Design," Engineering in Medicine and Biology Society, Proceedings of the 19th Annual International Conference of the IEEE, 6:2442-2444 (1997).
Jain et al., "Cell Therapy Attenuates Deleterious Ventricular Remodeling and Improves Cardiac Performance After Myocardial Infarction," Circulation 103:1920-1927 (2001).
Jalife, "Rotors and Spiral Waves in Atrial Fibrillation," Journal of Cardiovascular Electrophysiology 14:776-780 (2003).
Jané et al., "Alignment Methods for Averaging of High-Resolution Cardiac Signals: A Comparative Study of Performance," IEEE Transactions on Biomedical Engineering 38(6):571-579 (1991).
Jia et al., "Electrophysiologic Endocardial Mapping From a Noncontact Nonexpandable Catheter: A Validation Study of a Geometry-Based Concept," Journal of Cardiovascular Electrophysiology 11:1238-1251 (2000).
Kikuchi et al., "Targeted Modification of Atrial Electrophysiology by Homogeneous Transmural Atrial Gene Transfer," Circulation 111:264-270 (2005).
Kistler et al., "Validation of Three-Dimensional Cardiac Image Integration: Use of Integrated CT Image into Electroanatomic Mapping System to Perform a Catheter Ablation of Atrial Fibrillation," Journal of Cardiovascular Electrophysiology 17:341-348 (2006).
Kun et al., "Conductance Volumetric Model of an Eccentrically Positioned Catheter Within a Three-Compartment Ellipsoidal Ventricle," IEEE Transactions on Biomedical Engineering 40(6):589-592 (1993).
Laciar et al., "Improved Alignment Method for Noisy High-Resolution ECG and Holter Records Using Multiscale Cross-Correlation," IEEE Transactions on Biomedical Engineering 50(3):344-353 (2003).
Liu et al., "Endocardial Potential Mapping From a Noncontact Nonexpandable Catheter: A Feasibility Study," Annals of Biomedical Engineering 26:994-1009 (1998).
Lorensen et al. "Marching Cubes: A High Resolution 3D Surface Construction Algorithm," Computer Graphics 21(4):163-169 (1987).
Mäkelä et al., "A Review of Cardiac Image Registration Methods," IEEE Transactions on Medical Imaging 21(9):1011-1021 (2002).
Malladi et al., "A Geometric Approach to Segmentation and Analysis of 3D Medical Images," Mathematical Methods in Biomedical Image Analysis, Proceedings of MMBIA pp. 244-252 (1996).
Mangan et al., "Partitioning 3D Surface Meshes Using Watershed Segmentation," IEEE Transactions on Visualization and Computer Graphics 5(4):308-321 (1999).
Meininger et al., "Initial Experience with a Novel Focused Ultrasound Ablation System for Ring Ablation Outside the Pulmonary Vein," Journal of Interventional Cardiac Electrophysiology 8:141-148 (2003).
Merrill et al., "Electrical stimulation of excitable tissue: design of efficacious and safe protocols," Journal of Neuroscience Methods 141:171-198 (2005).
Miller, "Application of Registration for Ablation: A Marriage of Technologies," Journal of Interventional Cardiac Electrophysiology 11:87-89 (2004).
Nademanee et al., "A New Approach for Catheter Ablation of Atrial Fibrillation: Mapping of the Electrophysiologic Substrate," Journal of the American College of Cardiology 43(11):2044-2053 (2004).
Noseworthy et al., "The Impact of Respiration on Left Atrial and Pulmonary Venous Anatomy: Implications for Image-Guided Intervention," Heart Rhythm 2:1173-1178 (2005).
Pappone et al., "Robotic Magnetic Navigation for Atrial Fibrillation Ablation," Journal of the American College of Cardiology 47(7):1390-1400 (2006).
Paragios, "A Level Set Approach for Shape-Driven Segmentation and Tracking of the Left Ventricle," IEEE Transactions on Medical Imaging 22(6):773-776 (2003).
Persson et al., "A Simple Mesh Generator in MATLAB," SIAM Review 46(2):329-345 (2004).
Persson, "Mesh Generation for Implicit Geometries," Massachusetts Institute of Technology—Thesis, Feb. 2005.
Pham et al., "Current Methods in Medical Image Segmentation," Annu. Rev. Biomed. Eng. 2:315-337 (2000).
Rao et al., "Novel Noncontact Catheter System for Endocardial Electrical and Anatomical Imaging," Annals of Biomedical Engineering 32(4):573-584 (2004).
Reddy et al., "Integration of Cardiac Magnetic Resonance Imaging With Three-Dimensional Electroanatomic Mapping to Guide Left Ventricular Catheter Manipulation—Feasibility in a Porcine Model of Healed Myocardial Infarction," Journal of the American College of Cardiology 44(11):2202-2213 (2004).
Reddy et al., "Use of a Diode Laser Balloon Ablation Catheter to Generate Circumferential Pulmonary Venous Lesions in an Open-Thoracotomy Caprine Model," PACE 27:52-57 (2004).
Sanders et al., "Spectral Analysis Identifies Sites of High-Frequency Activity Maintaining Atrial Fibrillation in Humans," Circulation 112:789-797 (2005).
Sethian, "Level Set Methods and Fast Marching Methods: Evolving Interfaces in Computational Geometry, Fluid Mechanics, Computer Vision, and Materials Science," Department of Mathematics—University of California, Berkeley. Cambridge University Press, 1999.
Simon et al., "Electroanatomic Mapping of the Right Atrium With a Right Atrial Basket Catheter and Three-Dimensional Intracardiac Echocardiography," PACE 27:318-326 (2004).
Smits et al., "Catheter-Based Intramyocarial Injection of Autologous Skeletal Myoblasts as a Primary Treatment of Ischemic Heart Failure," Journal of the American College of Cardiology 42(12):2063-2069 (2003).
Solomon et al., "Real-Time Cardiac Catheter Navigation on Three-Dimensional CT Images," Journal of Interventional Cardiac Electrophysiology 8:27-36 (2003).
Sra et al, "Registration of 3D Computed Tomographic Images With Interventional Systems: Implications for Catheter Ablation of Atrial Fibrillation," J Interv Card Electrophysiol 16:141-148 (2006).
Sra et al., "Registration of Three-Dimensional Left Atrial Computed Tomographic Images With Projection Images Obtained Using Fluoroscopy," Circulation 112:3763-3768 (2005).
Stevenson, "Radiofrequency Catheter Ablation of Ventricular Tachycardia After Myocardial Infarction," Circulation 98:308-314 (1998).
Taccardi et al., "A New Intracavitary Probe for Detecting the Site of the Origin of Ectopic Ventricular Beats During One Cardiac Cycle," Circulation 75(1):272-281 (1987).
Thal et al., "Novel Applications in Catheter Ablation," Journal of Interventional Cardiac Electrophysiology 13:17-21 (2005).

(56) References Cited

OTHER PUBLICATIONS

Thiagalingam et al., "Noncontact Mapping of the Left Ventricle: Insights from Validation With Transmural Contact Mapping," PACE 27:570-578 (2004).

Voth, "The Inverse Problem of Electrocardiography: Industrial Solutions and Simulations," BEM and NFSI Conference Proceedings, Minneapolis, MN, May 12-15, 2005, pp. 191-194.

Wittkampf et al., "New Technique for Real-Time 3-Dimensional Localization of Regular Intracardiac Electrodes," Circulation 99:1312-1317 (1999).

Yezzi et al., "A Geometric Snake Model for Segmentation," IEEE Transactions on Medical Imaging 16(2):199-209 (1997).

Authorized officer Blaine R. Copenheaver, International Search Report/Written Opinion in PCT/US2011/032400 mailed Jun. 28, 2011, 8 pages.

Authorized officer, Dorothée Mülhausen, International Preliminary Report on Patentability in PCT/US2009/036099, mailed Oct. 14, 2010, 20 pages.

Authorized officer Nora Lindner, International Preliminary Report on Patentability in PCT/US2009/061277 mailed May 12, 2011, 12 pages.

Authorized officer Yoshiko Kuwahara, International Preliminary Report on Patentability in PCT/US2008/013553 mailed Jul. 8, 2010, 7 pages.

Authorized officer, Blaine R. Copenheaver, International Search Report and Written Opinion in PCT/US2009/061277, mailed Apr. 8, 2010, 13 pages.

Examination Report, AU Application No. 2011253403, mailed Jan. 22, 2013, 4 pages.

\* cited by examiner

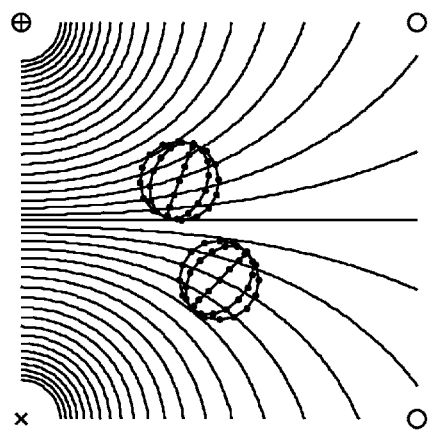
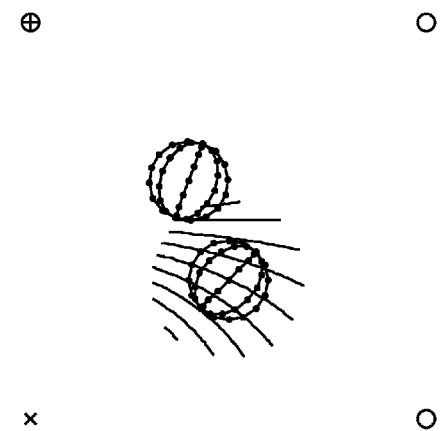
FIG. 7A  FIG. 7B
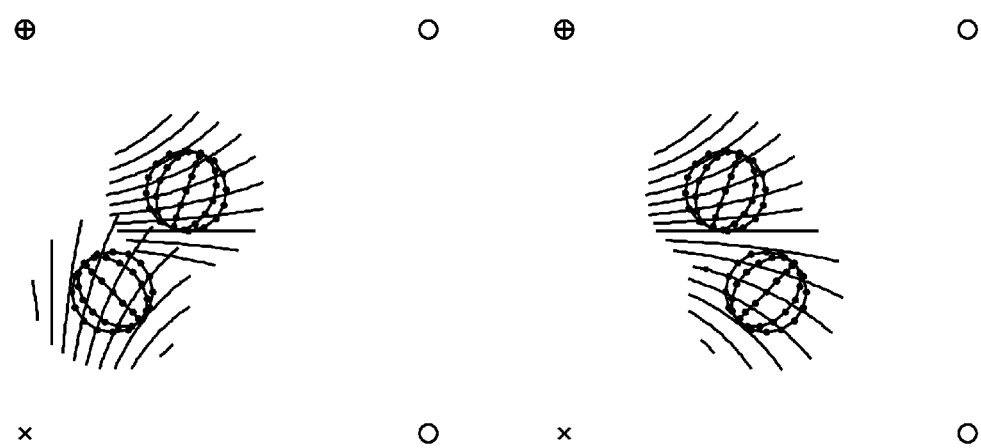
FIG. 7C  FIG. 7D

TRACKING USING FIELD MAPPING

TECHNICAL FIELD

This invention relates to determining the position of an object, such as tracking the position of one or more catheters in a patient's heart cavity.

BACKGROUND

Use of minimally invasive procedures, such as catheter ablation, to treat a variety of heart conditions, such as supraventricular and ventricular arrhythmias, is becoming increasingly more prevalent. Such procedures involve the mapping of electrical activity in the heart (e.g., based on cardiac signals), such as at various locations on the endocardium surface ("cardiac mapping"), to identify the site of origin of the arrhythmia followed by a targeted ablation of the site. To perform such cardiac mapping a catheter with one or more electrodes can be inserted into the patient's heart chamber.

Under some circumstances, the location of the catheter in the heart chamber is determined using a tracking system. Catheter tracking is a core functionality of modern mapping systems that also include software and graphic user interface to project electrical data on 3D renderings of cardiac chambers. Currently there are several tracking systems available, some more useful and commonly used than others. Some systems are based on the use of magnetic or electric fields from external sources to sense and track the location of the catheter. Some are based on the use of magnetic or electric fields sources mounted on the tracked catheters.

SUMMARY

In some aspects, a method includes causing current to flow among multiple current injecting electrodes, at least some of the current injecting electrodes being placed in stable locations inside a patient's body to generate a field in an organ. The method also includes, in response to the current flow caused by the current injecting electrodes, measuring a signal at each of multiple measuring electrodes on a catheter for each of multiple locations of the catheter. The method also includes determining expected signals at additional locations within the organ based on the measured signals and determining a position of at least one of the measuring electrodes of the catheter and/or a measuring electrode of another catheter in the organ based on at least the expected signals.

Embodiments can include one or more of the following.

The current injecting electrodes are not on the catheter that includes the measuring electrodes.

Determining the expected signals can include determining expected signals in the absence of information from an external tracking system.

Determining the expected signals can include determining relative locations of the plurality of measuring electrodes at different ones of the multiple locations in the organ based on the measured signals.

Determining the relative locations can include reconciling fields measured at the different ones of the multiple locations.

Reconciling the fields can include using a cost minimization function on one or more of a point, multiple points, a surface, and a volume.

Determining the relative locations can include determining a translation and rotation between the plurality of measuring electrodes at the multiple locations.

The measured signals for the catheter at each location can define a corresponding set of measurements and determining the expected signals can include combining information from the different sets to determine a field map indicative of the expected signals at the additional locations.

Combining can include aligning the information from the different sets to account for the different locations of the catheter based on the known relative locations of the measuring electrodes on the catheter.

The information from each of the sets of measurements can be a local field map.

Determining the expected signals can include reconciling the local field maps from the multiple locations.

Reconciling the local field maps can include using a cost minimization function on one or more of a point, a surface, and a volume.

Reconciling the local field maps can include determining a translation and rotation between the plurality of the local field maps.

Determining the expected signals can include determining the expected signals based on the measured signals and known relative locations between the multiple measuring electrodes on the catheter.

The expected signals can be a field map.

The field map can be a differentiable function.

Determining the expected signals can include using Laplace's equation, Poisson's equation, and/or a polynomial estimation.

The current injecting electrodes can be mounted on one or more catheters that are secured inside the organ.

The current injecting electrodes can include both electrodes mounted on one or more catheters secured inside the organ and one or more body-surface electrodes.

Measuring the signal can include measuring potentials.

Measuring the signal at the multiple locations can include moving the catheter to the multiple locations within the organ, and using the measuring electrodes to measure signals for each of the multiple locations of the catheter.

Determining expected signals can include for the multiple locations, modeling portions of the field using the measured signals from the one or more measuring electrodes to generate multiple models of portions of the field and combining the multiple models to generate a combined field model.

Combining the multiple models can include sequentially combining the multiple models to generate the combined model of the field.

Combining the multiple models can include concurrently combining the multiple models to generate the combined model of the field.

The combined field model can include a weighted mean of the multiple models of the portions of the field.

The method can also include removing the measuring electrodes from the organ and subsequent to removing the measuring electrodes from the organ using the expected signal measurements to track a location of the measuring electrode of the another catheter.

The current-injecting electrodes can include at least three sets of current injecting electrodes, and wherein the causing of the current flow includes causing current to flow between each set of current injecting electrodes.

The organ can be the patient's heart.

Determining the position can include determining the position of the measuring electrode of the another catheter with the another catheter being a separate catheter from the catheter that includes the multiple measuring electrodes.

The measured signals and expected signals can be processed to account for respiration and heart beat.

Processing the measured signals and expected signals can include using information from a catheter electrode positioned in a stable location relative to the organ.

The stable location can be the coronary sinus.

In some additional aspects, a system includes a catheter configured for insertion into an organ in a patient's body and includes multiple measuring electrodes. The system also includes multiple current injecting electrodes placed in stable locations inside a patient's body to generate a field in an organ. The system also includes an electronic control system coupled to the multiple current injecting electrodes and to the measuring electrodes. The electronic control system is configured to cause current to flow among multiple current injecting electrodes to generate a field in an organ and to measure the field and, in response to the current flow caused by the current injecting electrodes, measure a signal at each of the multiple measuring electrodes for each of multiple locations of the catheter. The system also includes a processing system coupled to the electronic system. The processing system is configured to determine expected signals at additional locations within the organ based on the measured signals and determine a position of at least one of the measuring electrodes of the catheter and/or a measuring electrode of another catheter in the organ based on at least the expected signals.

Embodiments can include one or more of the following.

The current injecting electrodes can be mounted on one or more catheters that are secured inside the organ.

The measuring electrodes mounted on the catheter can include electrodes that can be moved and positioned at multiple locations in an organ.

The current-injecting electrodes can include at least three sets of current injecting electrodes.

The current injecting electrodes are not on the catheter that includes the measuring electrodes.

The processing system can be further configured to determine the expected signals in the absence of information from an external tracking system.

The processing system can be further configured to determine relative locations of the plurality of measuring electrodes at different ones of the multiple locations in the organ based on the measured signals.

The processing system can be further configured to reconcile fields measured at the different ones of the multiple locations using a cost minimization function.

The processing system can be further configured to determine a translation and rotation between the plurality of measuring electrodes at the multiple locations.

The measured signals for the catheter at each location define a corresponding set of measurements and the processing system can be further configured determine the expected signals by combining information from the different sets to determine a field map indicative of the expected signals at the additional locations.

The processing system can be further configured to combine the information from the different sets to determine a field map by aligning the information from the different sets to account for the different locations of the catheter based on the known relative locations of the measuring electrodes on the catheter.

The expected signals can be a field map.

The processing system can be further configured to determine the expected signals using Laplace's equation, Poisson's equation, and/or a polynomial estimation.

The current injecting electrodes can include both electrodes mounted on one or more catheters secured inside the organ and one or more body-surface electrodes.

The processing system can be further configured to use the expected signal measurements to track a location of the measuring electrode of the another catheter.

The processing system can be further configured to process the measured signals and expected signals to account for respiration and heart beat.

In some additional aspects, a method includes generating a baseline signal measurement by causing current to flow among multiple current injecting electrodes at least some of the current injecting electrodes being placed in stable locations inside a patient's body to generate a field in an organ and in response to the current flow, measuring a signal at one or more measuring electrodes positioned at one or more secure locations. The method also includes subsequent to generating the baseline signal measurement, causing current to flow among the multiple current injecting electrodes, in response to the current flow, measuring a signal at the one or more measuring electrodes, and comparing the measured signal to the baseline signal to generate a comparison result.

Embodiments can include one or more of the following.

The method can also include determining whether a location of the multiple current injecting electrodes inside the patient's body has changed based on the comparison result.

The method can also include providing an audio or visual indicator upon determining that the location of the multiple current injecting electrodes has changed.

The one or more measuring electrodes can be one or more ECG leads.

The one or more measuring electrodes can be one or more body surface electrodes.

The method can also include, subsequent to generating the baseline signal measurement, in response to the current flow, measuring a signal at each of multiple measuring electrodes on a catheter for each of multiple locations of the catheter and determining expected signals for the measuring electrodes at additional locations within the organ based on the measured signals.

The method can also include, subsequent to generating the baseline signal measurement, in response to the current flow, measuring a signal at each of multiple measuring electrodes on a catheter and determining a relative location of the catheter based on the signals measured by the multiple measuring electrodes on the catheter.

The one or more measuring electrodes can include one or more stable intracardiac electrodes.

The organ can be a patient's heart.

Generating the baseline signal measurement can include compensating for respiration and heartbeat of the patient.

Comparing the measured field to the baseline signal can include calculating a residual norm between the baseline signal and the measured signal.

Comparing the measured field to the baseline signal can include comparing the residual norm to a threshold value.

The method can also include providing information to enable a clinician to guide the current injecting electrodes to a location where the baseline signal measurement was generated.

Comparing the measured field to the baseline signal can include calculating a displacement trajectory.

The displacement trajectory can provide a three-dimensional model providing an indication of a current location of the current injecting electrodes and an indication of the location where the baseline signal measurement was generated.

In some aspects, a system includes one or more measuring electrodes positioned at one or more secure locations and multiple current injecting electrodes at least some of the current injecting electrodes being placed in stable locations inside a patient's body to generate a field in an organ. The system also includes an electronic control system coupled to the multiple current injecting electrodes and to the one or more measuring electrodes. The electronic control system is configured to cause current to flow among multiple current injecting electrodes and, in response to the current flow, measure a signal at the one or more measuring electrodes. The system also includes a processing system coupled to the electronic system. The processing system is configured to generate a baseline signal measurement, subsequent to generation of the baseline signal measurement, compare a measured signal from the one or more measuring electrodes to the baseline signal to generate a comparison result, and determine whether a location of the multiple current injecting electrodes inside the patient's body has changed based on the comparison result.

Embodiments can include one or more of the following.

The system can also include an indicator configured to provide an audio or visual indication upon determining that the location of the multiple current injecting electrodes has changed.

The one or more measuring electrodes can be one or more ECG leads.

The one or more measuring electrodes can be one or more body surface electrodes.

The system can also include multiple measuring electrodes on a catheter. The electronic control system can be further configured to measure a signal at each of multiple measuring electrodes on the catheter for each of multiple locations of the catheter and the processing system can be further configured to determine expected signals for the measuring electrodes at additional locations within the organ based on the measured signals.

The processing system can be further configured to determine a relative location of another catheter based on the signals measured by the multiple measuring electrodes on the catheter.

The one or more measuring electrodes can be one or more stable intracardiac electrodes.

The processing system can be further configured to compensate for respiration and heartbeat.

The processing system can be further configured to compare the measured field to the baseline signal using a residual norm between the baseline signal and the measured signal.

The processing system can be further configured to compare the measured field to the baseline signal by comparing the residual norm to a threshold value.

The system can also include a display unit configured to provide information to enable a clinician to guide the current injecting electrodes to a location where the baseline signal measurement was generated.

The system can also include a display unit configured to display a displacement trajectory.

The displacement trajectory can provide a three-dimensional model providing an indication of a current location of the current injecting electrodes and an indication of the location where the baseline signal measurement was generated.

Embodiments of the systems and methods described herein may also include devices, software, components, and/or systems to perform any features described above in connection with methods and systems described herein.

Embodiments of the methods and systems generally disclosed herein can be applied to determining the position of any object within an organ in a patient's body such as the patient's heart, lungs, brain, or liver.

As used herein, the "position" of an object means information about one or more of the 6 degrees of freedom that completely define the location and orientation of a three-dimensional object in a three-dimensional coordinate system. For example, the position of the object can include: three independent values indicative of the coordinates of a point of the object in a Cartesian coordinate system and three independent values indicative of the angles for the orientation of the object about each of the Cartesian axes; or any subset of such values.

As used herein, "heart cavity" means the heart and surrounding tissue.

Unless otherwise defined, all technical and scientific terms used herein have the same meaning as commonly understood by one of ordinary skill in the art to which this invention belongs. In case of conflict with documents incorporated herein by reference, the present document controls.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIGS. 7A, 7B, 7C, and 7D are exemplary field models.

Like reference symbols in the various drawings indicate like elements.

DETAILED DESCRIPTION

Figure 1:
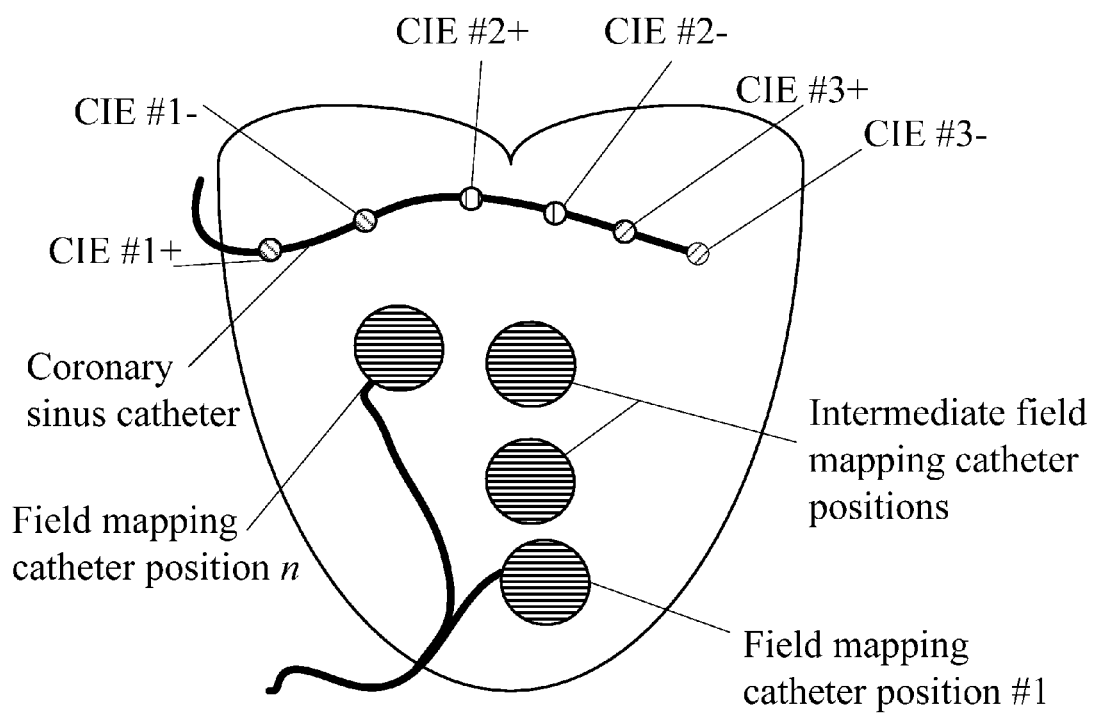
FIG. 1 is an exemplary schematic diagram of an arrangement for positioning current injection electrodes (CIE) and potential measuring electrodes (PME) with respect to a patient's heart cavity.

Embodiments disclosed herein include a method and system for generating a model of the field that provides expected signal measurements of the field at various locations within the heart cavity and determining the position of a catheter in a patient's heart cavity using the determined model of the field.

More particularly, the methods and systems described herein provide a method for tracking electrodes mounted on catheters within and relative to the cardiac cavity, including any number of chambers within this cavity and the blood vessels surrounding it, but it can be used for tracking catheters in other body organs as well. Electrodes can be mounted on one or multiple catheters and by tracking these electrodes the location of such catheters can be determined and the catheters can be tracked. By knowing the physical characteristics of a catheter and the position of the electrodes on it, it is possible to track specific portions of the catheter (e.g. the distal section) or to determine the shape and the orientation of the catheter (e.g. by using a spline fitting method on the location of multiple electrodes of the same catheter). Electrodes can also be mounted on other devices that require tracking inside the heart cavity.

In some examples, the system tracks the location of the electrodes and catheters by generating a multitude of fields using field generating devices (FGD) positioned and secured in stable locations internally (e.g., field generating devices secured in the coronary sinus, atrial appendage, and/or apex) or externally (e.g., field generating devices secured on back, chest, or other body surface) and using measurements of the same fields on electrodes mounted on other catheters to locate them. In general, a FGD can be an element or device which can create a measurable field of some type, e.g., potential, magnetic, acoustic, etc. One implementation of the system uses current injecting electrodes (CIE) to create potential fields and uses potential measuring electrodes (PME) to measure the fields. In general, a CIE can be an element which generates a potential field by injecting current into the area of interest, a CIE is paired with an element providing a sink for the current, and a PME can be an electrode which can measure a potential field. However, the methods and approaches described herein can be applied to systems and methods using magnetic fields, acoustic fields, or other measurable fields.

The disclosed invention does not require but may use any external patches attached to the body, or any other external energy emitter. However, the invention works even if only internal field generators are available, and it does not require any knowledge about the location in space of any field generator. In some embodiments, field generation may use objects that are secured to the heart itself, reducing inaccuracies from motion artifacts that are experienced by systems that are referenced to an external coordinate system or are affected by relative motion between the field generator and the heart (e.g. skin to heart). The system also incorporates methods for detecting when the field generators have altered location and for guiding the user in repositioning them.

In general, in one aspect, a catheter that includes one or more potential measuring electrodes (PME) that can measure the fields (e.g., measure potentials in the heart cavity in response to the current provided by the CIEs) is used for generating a field map. The field map provides expected signal measurements of the field at various locations within the heart cavity. In some embodiments, it is not necessary for the field mapping catheter to be tracked by an independent tracking system.

Once a field map is generated, the catheter used to generate the field map can optionally be taken out of the body. However, the CIE used to generate the fields are left in their stable locations for subsequent use in tracking other electrodes. Using the field map it is possible to determine the location of any potential measuring electrodes (PME) that can measure the generated fields (e.g., the fields generated using the current injecting electrodes) inside the volume covered by the field map. The position of a tracked PME is determined by comparing the measured field value and the modeled field values. The position in the field map that holds a value matching the measurement of the tracked PME is assigned as the location of that PME.

In the above discussion and in the details that follow, the focus is on determining the position of one or more catheters in a heart cavity for diagnosis and treatment of cardiac arrhythmias. However, this is only an exemplary application. The method and system generally disclosed herein could be used to track essentially any catheter mounted with at least one electrode, regardless of the catheter's intended function. Relevant examples include endocardial biopsies, therapies involving intra-myocardial injections of cells, drugs, or growth factors, and the percutaneous placement cardiac valves. In other examples, the method and systems generally disclosed herein can be applied to determining the position of any object within any distribution of materials characterized by a conductivity profile. For example, the methods and systems generally disclosed herein can be applied to determining the position of any object within an organ in a patient's body such as the patient's heart, lungs, brain, or liver.

FIG. 1 shows an exemplary schematic diagram of an arrangement for positioning current injection electrodes (CIE) and a field mapping catheter with respect to a patient's heart cavity. It shows three CIE pairs (e.g., $CIE_{1+}$-$CIE_{1-}$; $CIE_{2+}$-$CIE_{2-}$; and $CIE_{3+}$-$CIE_{3-}$) mounted on electrodes on a single catheter placed in the coronary sinus, which act as field generating devices. As described herein, while shown as positioned in the coronary sinus, other locations outside of the heart chamber, within the organ itself, and/or outside of the patient's body could be used to secure the CIE pairs.

A field mapping catheter (FMC) is placed within the cardiac chamber and can move relative to the cardiac chamber. One exemplary FMC is a catheter with at least four non-planar field measuring sensors. The FMC is able to measure the fields generated by the different CIE pairs. The spatially diverse field measurements allow the field in the region around the catheter to be modeled and predicted. FIG. 1 shows multiple locations of the FMC (e.g., Field mapping catheter positions 1 . . . n) as the FMC moves through a cardiac chamber and measures the fields across different locations.

Field mapping is performed in order to generate a complete representation of the fields within which electrodes and catheters can be tracked. Field mapping involves the collection of measurements of the fields generated by the FGD at one or more distinct times and across one or more distinct locations. The measurements are collected by one or more field mapping catheters (FMC). The FMC measurements are combined with information about relative FMC locations to create the field map that is used for tracking electrodes and catheters.

If the FMC contains four or more electrodes not entirely contained in a plane, its measurements can be used to generate a local field model, that is, an estimate of the potential measurements in the volume surrounding the FMC for each of the fields generated by the FGD.

Figure 2A:
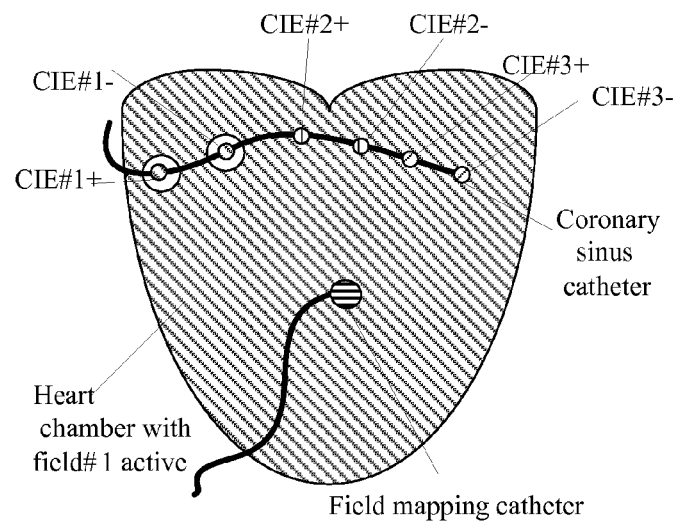
FIGS. 2A, 2B, and 2C are diagrams of exemplary fields generated by multiple CIE configurations and measured by a field mapping catheter (FMC).
Figure 2B:
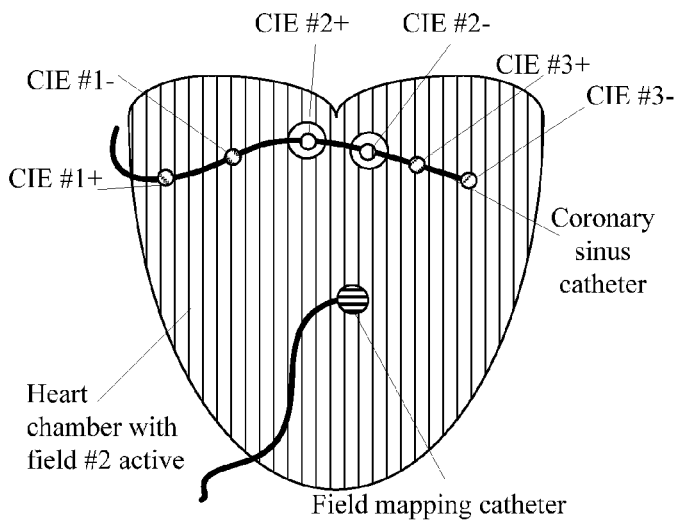
Figure 2C:
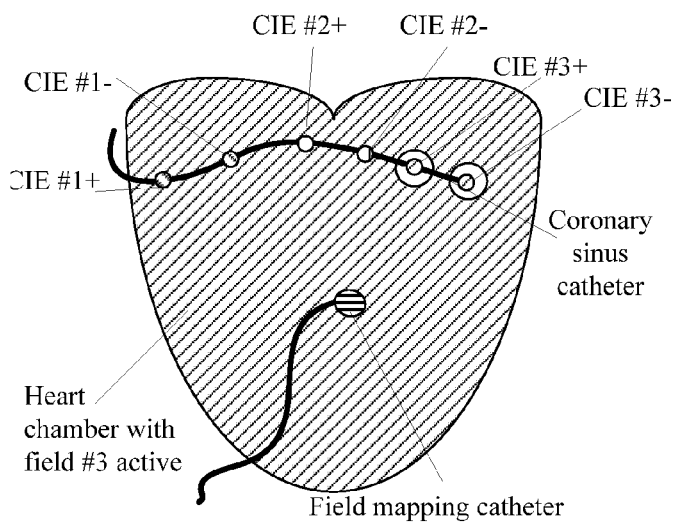

As shown in FIGS. 2A-2C, for a particular location of the FMC, the FGD generate multiple fields (e.g., by using different ones of the CIE pairs $CIE_{1+}$-$CIE_{1-}$; $CIE_{2+}$-$CIE_{2-}$; and $CIE_{3+}$-$CIE_{3-}$), each of which can be modeled in a region surrounding the FMC. Local field models (e.g., local models of expected signal measurements in a region surrounding the FMC) made at multiple different locations of the FMC can then be combined into the field maps (e.g., expected signal measurements of the field at various locations within the heart cavity) required by the tracking system. The model of the field can be determined, for example, by solving Laplace's equation in a homogeneous medium representing the cardiac chamber to generate the local field models or the field map. In some additional examples, the model of the field can be determined using other mathematical methods for characterizing the fields, e.g., interpolation and extrapolation of measured values or fitting to a parametric model. The combination of techniques can be used to generate a field map that is accurate in areas that are not specifically probed by the FMC and even in areas not lying between positions that were probed.

In order to combine individual FMC measurements (e.g., measurements collected at different positions within the organ) to generate the field map, the relative locations at which the measurements were collected are used. One method of determining FMC locations is by using an independent tracking system. Such systems are known in the art and may use magnetic or acoustics fields to determine location of a sensor, such as the method disclosed, for example, in U.S. patent application Ser. No. 12/258,688 entitled "TRACKING SYSTEM USING FIELD MAPPING" and filed Oct. 27, 2008, the contents of which is incorporated by reference herein. In contrast to methods using an independent tracking system, methods of determining relative FMC locations described herein involve reconciling the local field models corresponding to the FMC measurements. Reconciling two or more local field models may involve minimizing a cost function on a point, surface, volume or combination of these within the intersection of volumes described by the separate models. Model reconciliation can also make use of a priori information about the expected characteristics of the field or the shape of the FMC.

The field map can be generated using the FMC measurements and their relative locations. The field map can be a weighted mean of the local field models such that the local field models from the nearest FMC positions have the greatest impact on the field map. Another option is to generate the field map using all of the FMC electrode locations and measurements in a method analogous to how a local field model is generated. The complete set of locations can be used to solve the inverse Laplace problem, or mathematical methods may be used to interpolate the measurements or fit them to a parametric model.

In general, the field map generated can be represented by a differentiable function. The tracking algorithm, which matches an electrode's measurements with a location in the field map, requires finding a minimum in a cost function using optimization. Optimization techniques of differentiable functions are faster and more accurate than other techniques, giving another advantage to the disclosed invention.

Once a sufficiently accurate and complete field map is generated, the FMC can be removed from the body. This may be advantageous when it is desired to have fewer catheters inside the body organ for clinical reasons. Alternatively, the FMC may remain in the body while one or more other catheters are tracked based on the field map generated using the FMC.

Using the field map, it is possible to determine the location of any PME that can measure the generated fields inside the volume covered by the field map.

Figure 3A:
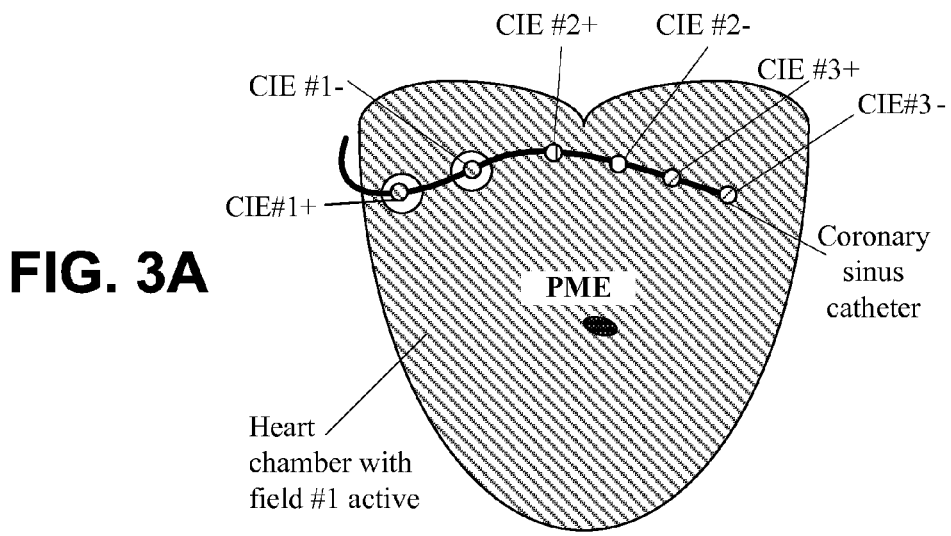
FIGS. 3A, 3B, and 3C are exemplary fields generated by multiple CIE configurations and measured by a potential measuring electrode (PME).
Figure 3B:
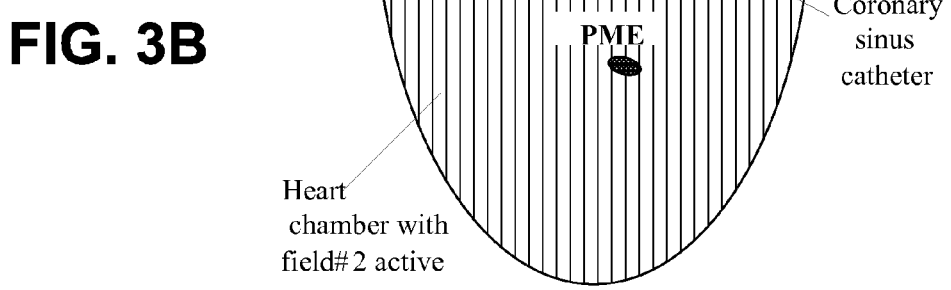
Figure 3C:
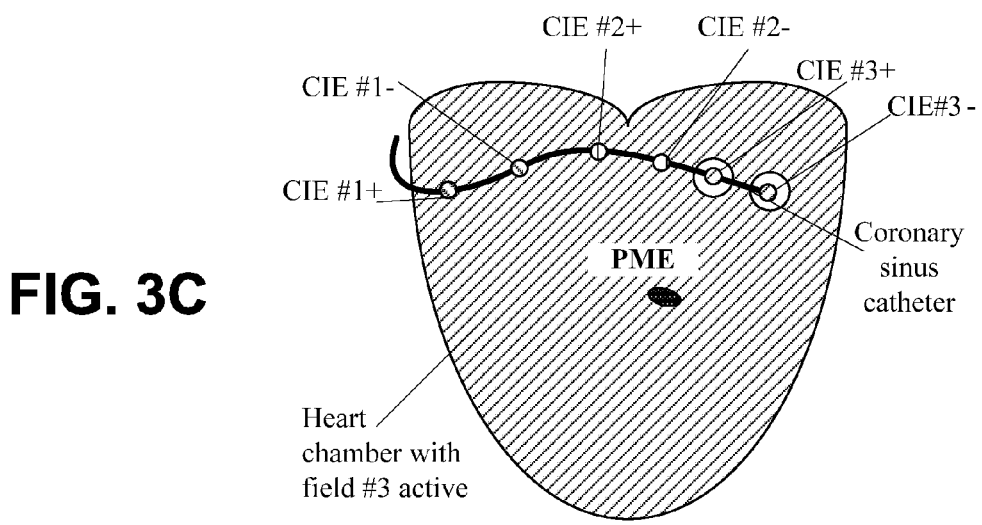

FIGS. 3A-3C show an exemplary PME exposed to the three fields of the schematic system (e.g., the fields generated by the three different pairs of CIE). Using the field map of the same fields, the tracking processor can identify the unique position in the chamber which would cause the PME to measure the three observed potentials. The tracking processor may improve tracking performance by incorporating any a priori information about a catheter, e.g., catheter geometry (e.g. electrode dimensions and inter-electrode distance) or catheter dynamics (e.g. material properties or known shapes).

Using the field map, the system can track sensors inside a body without having these sensors emit any field that needs to be detected. That is, the CIE used to generate the field are active, while the tracked PME are passive. In contrast, systems that require the tracked electrode to be active often track a single electrode at any given time. For the tracking of multiple electrodes, such systems usually activate one electrode at a time and sequentially cycle through all tracked electrodes. Since there is a minimum duration that each electrode needs to be active in such a system, and there is also a desired refreshing rate for the tracked location, there is a limit to the number of electrodes that can be tracked simultaneously in such systems. Due to the passive nature of the tracked PME in the systems and methods described herein, there is no limit to the number of PMEs that can be tracked simultaneously.

Additionally, in some aspects, the systems and methods described herein provide a method to monitor the location stability of the FGD using cutaneous patches (e.g., ECG leads) and intracardiac electrodes. In case the FGD is displaced, the system can enable the clinician to reposition the FGD appropriately.

Field Generation and Measurement

Referring back to FIG. 1, FIG. 1 shows an exemplary schematic diagram of an arrangement for positioning multiple current injection electrodes (CIE) mounted on one or more catheters. The CIE are located in a stable position in the heart and are secured in a way that minimizes relative movement between the electrodes and the heart walls. This can be done either by choosing a location such that the catheter will conform to the anatomy and will stay in a fixed position (e.g., coronary sinus, appendage or apex), or by using a fixation mechanism (e.g. screw-in lead or balloon mechanism).

In general, in order to inject current an electrode must have impedance that is low enough for the current driver to overcome (e.g. 5 k$\Omega$). Low impedance can be achieved by a sufficient surface area or by using materials or coatings that lower the impedance of the electrode. It should be noted that any sufficiently low impedance electrode can be used for current injection, and in a case where many or all electrodes on a certain catheter are capable of injecting current, the designation of such electrodes as CIE only indicates that these electrodes are actually being used for current injection.

In some embodiments, for example, as shown in FIG. 1, a set of 3 CIE configurations can be arranged to span three dimensional (3D) space and provide XYZ coordinates of other electrodes. Because the conductivity of the heart is inhomogeneous and varies across frequency, it is also possible to create a potential field with sufficient spatial diversity using fewer CIE configurations. An example of a CIE configuration is a pair of CIE configured as a dipole, having one CIE acting as a current source and the other CIE acting as a current sink. An electrode can be used in more than one CIE configuration. Ideally, the electrodes, are not all placed in the same plane so that a 3D space is clearly spanned. For this reason, in some embodiments, a minimum of 4 CIE configurations can be preferable.

Other configurations of CIE are possible as long as these configurations span the 3D space. Examples of such a configuration could be quadruples involving 4 CIE, or even a non-symmetric configuration involving 3 CIE. CM can be on the same catheter or on different catheters. They can be in the same chamber, in different chambers, in the cardiovascular system surrounding the heart or in other tissue. It is also possible to configure CIE such that current is sourced by intracardiac electrodes while a cutaneous patch acts as a sink. It should be understood that the distinction between source and sink is of no significance, in particular when the signal is modulated by a carrier frequency. For simplicity, a method using electrode pairs will be explained herein, but the same method can be applied using other configurations. In such cases there is a need for the electrode configurations to create a set of fields with sufficient spatial variety to uniquely locate the set of electrodes being tracked.

It should be appreciated that knowing the spatial configuration of CIEs is not required for the tracking system to operate as long as the pairs used for injecting the currents span the three-dimensional space of the chamber as described. The properties of the medium and the inhomogeneity of it are not modeled in any way, and no prior knowledge is required about the medium.

Pending patent application Ser. No. 12/061,297 entitled "Intracardiac Tracking System" and filed Apr. 2, 2008, whose disclosure is incorporated herein in its entirety by reference, describes an exemplary signal acquisition and generation module.

In the tracking system described herein, potential measuring electrodes (PMEs) mounted on tracked catheters measure both potentials from cardiac activation and the fields generated by the CIE. There is a need to separate the tracking signal being used for location determination from the cardiac signal being used for generating electrical activation maps. The CIE inject current at a frequency higher than cardiac activation (cardiac activation<2 kHz, CIE>4 kHz, e.g. 5 kHz) such that the two types of signals can be easily distinguished using frequency analysis. It should be noted that other methods for distinguishing between the CIE signal and the cardiac activation signal can be used, such as injecting a spread-spectrum signal having a low energy level in the frequency range of the cardiac activation signal, and detecting this spread-spectrum signal in the signal collected by the all PME.

In order to span the space, multiple CIE configurations must inject current (e.g. three pairs not residing in the same plane). There is a need to determine the source of the injected signal and to trace it to a specific CIE configuration. One implementation requires the pairs of CIE to inject current sequentially, one pair at a time, so that it is possible to trace the source of the measured PME signals to a specific pair. This is called time-division multiplexing. In the case of time-division multiplexing, CIE are activated in sequence such that at one point in time one pair is activated (e.g. $CEI_{1+}$ and $CEI_{1-}$) and at the next point in time another pair is activated (e.g. $CIE_{2+}$ and $CIE_{2-}$). The switching between pairs may occur every cycle (e.g. ⅕ kHz=200 μs) or every few cycles (e.g. 20 cycles, 20×200 μs=4 ms). It should be noted that frequency- or code-division (spread-spectrum) multiplexing, rather than time-division, may be used to separate the signals. In the case of frequency-division multiplexing, all CIE pairs may inject the current at the same time, but each pair uses a different signal frequency. The signal collected at the PME is filtered according to the frequency, and the signal measured in each frequency is then associated with the appropriate originating pair.

The relative impedance between blood and surrounding media varies over frequency. As a result, injecting current at the same CIE at multiple frequencies (e.g. 5 kHz and 30 kHz) results in different fields in the medium. This method can be used to diversify the fields obtained with the same electrodes. This is advantageous when trying to minimize the number and span of CIE.

While in some of the specific embodiments that follow the signals measured by the electrodes correspond to the relative strength (e.g., amplitude) of the measured electrical signal (e.g., potential), further embodiments may also analyze the phase of the measured signal, either alone or in combination with the amplitude of the measured signal. The phase of the measured signal is indicative of spatial variations in the imaginary part of the complex conductivity (e.g., permittivity) in the distribution of materials.

Field Mapping

In general, the system generates a set of expected signals based on the signals measured by the FMC. One example of a set of expected signals is a field map. A field map assigns scalar or vector measurements of the generated fields to positions in the volume within which electrodes and catheters will be tracked. The field map can be represented as a function, e.g., a differentiable function. In embodiments in which the absolute location of the FMC within the organ is not known, a location of the FMC in the initial measurement may define the origin and orientation of the coordinate frame for the field map. In general, a field is any measurable phenomenon that associates a scalar or vector value to points in space (e.g., to every point in space). PME can measure different kinds of scalar fields, such as electrical potential field (potential difference relative to a reference location), impedance field (impedance between every location and a reference location), etc.

The field mapping process uses a catheter that has at least four non-coplanar PMEs that can measure the fields generated by the cm. An exemplary catheter that can be used for the field mapping process is the MEA catheter described in pending patent application Ser. No. 12/005,975 entitled "Non contact mapping catheter" and filed Dec. 28, 1007, whose disclosure is incorporated herein in its entirety by reference. The catheter used is referred to as the field mapping catheter (FMC).

Figure 4:
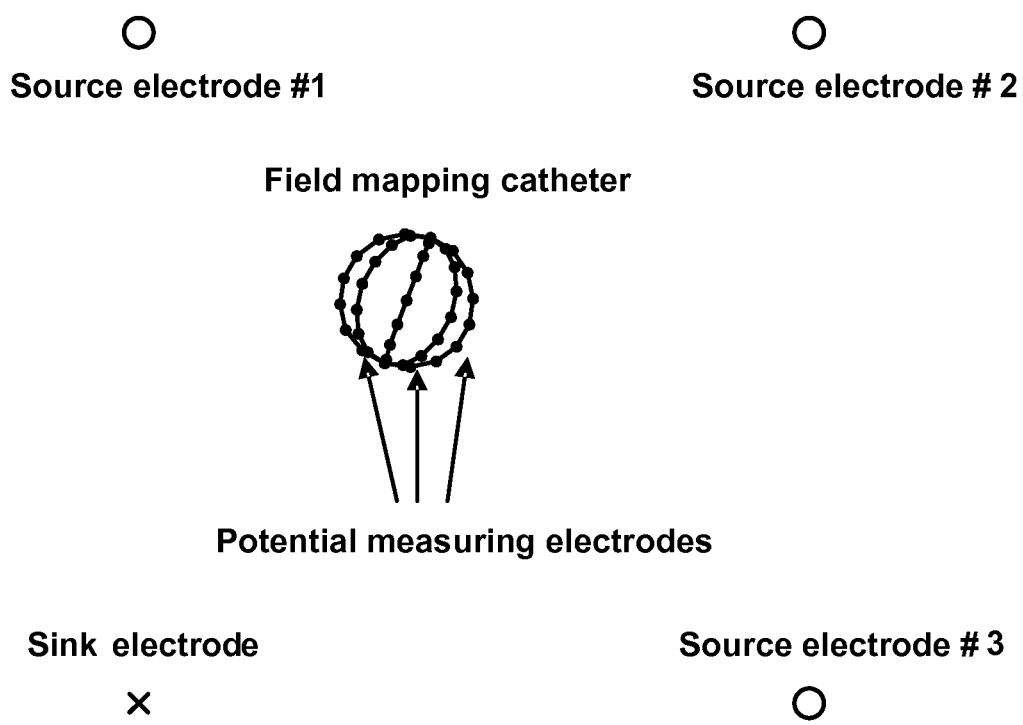
FIG. 4 is a schematic representation of the field mapping system

Referring now to FIG. 4, in an embodiment of the field mapping system using potential fields, FIG. 4 shows schematically a realization of the field mapping system. The system includes four electrodes (source electrode #1, source electrode #2, source electrode #3, and sink electrode). For clarity, this schematic shows the two-dimensional analog to the proposed field mapping system. A real system would locate the four CIE so that the CIE are not coplanar. The system also includes a field mapping catheter that includes multiple (e.g., at least four) non-coplanar PMEs.

Figure 5A:
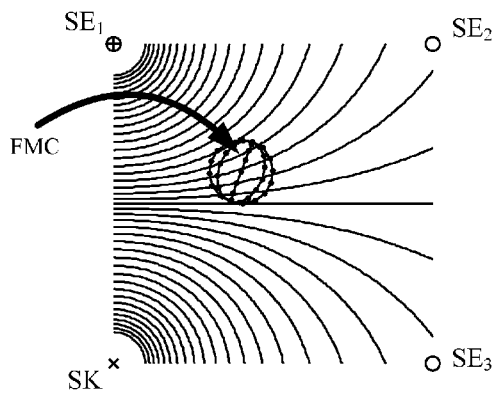
FIGS. 5A, 5B, and 5C are exemplary field diagrams.
Figure 5B:
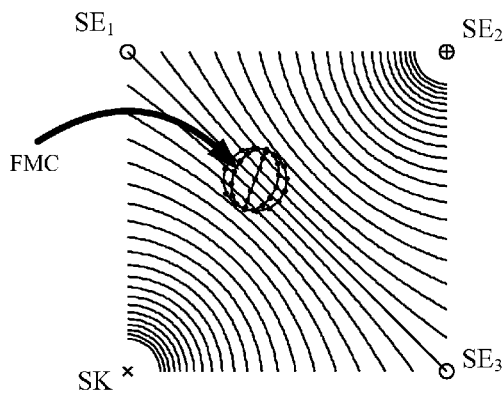
Figure 5C:
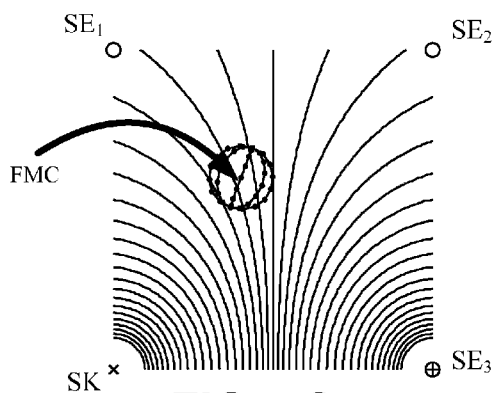

As shown in FIGS. 5A-5C, in operation, the FMC is initially placed somewhere within the region of interest (e.g., within the organ). The system causes current to flow among the multiple current injecting electrodes. For example, in the example shown in FIG. 5A the system causes current to flow between source electrode 1 ($SE_1$) and sink electrode (SK), in FIG. 5B the system causes current to flow between source electrode 2 ($SE_2$) and sink electrode (SK), and in FIG. 5C the system causes current to flow between source electrode 3 ($SE_3$) and sink electrode (SK). As shown in FIGS. 5A-5C, the field generated by each pair of electrodes is different based on the relative locations of the electrodes. In response to the current flow caused by the current injecting electrodes, the system measures signal at each of multiple measuring electrodes on a FMC. More particularly, the system measures the potentials for the field generated by each CIE pair at the distinct locations of its electrodes. The FMC can subsequently be moved to another location within the region of interest.

Figure 6A:
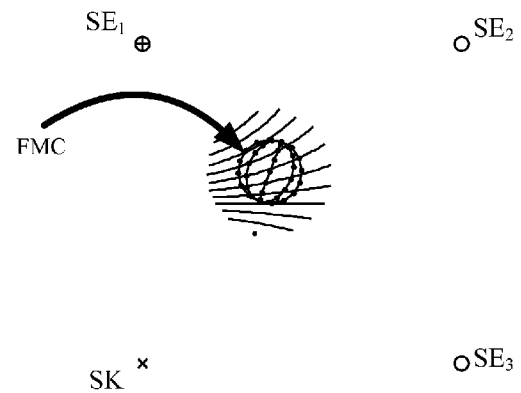
FIGS. 6A, 6B, and 6C are exemplary local field models associated with the fields shown in FIGS. 5A, 5B, and 5B.
Figure 6B:
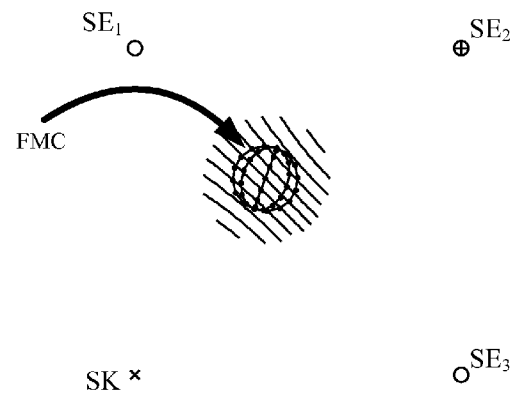
Figure 6C:
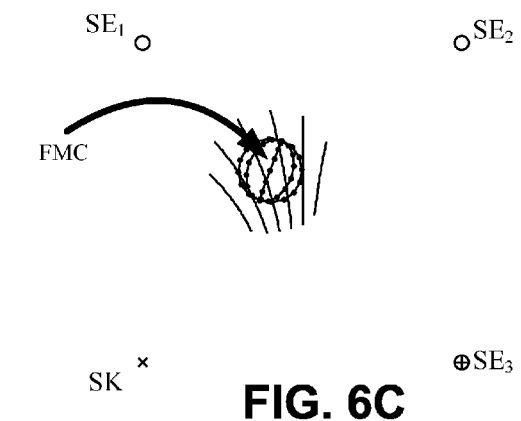

As shown in FIGS. 6A-6C, the signal measurements gathered by the measuring electrodes on a FMC allow the tracking processing unit to create a set of expected signal measurements that describe each field in a region around the FMC (referred to herein as a local field model). A local field model can be generated for each of the CIE pairs and for each location of the FMC. The system combines the multiple models to generate a combined field model that provides a set of expected signal measurements for a larger area of the organ than the area that is modeled by the local field models. The process for creating the local field model is described in more detail herein. The local field models are generated in the absence of information from an external tracking system.

The relative positions of the FMC at different locations can be determined based on the signal measurements gathered by the measuring electrodes on a FMC at the different locations. More particularly, the structure of each field allows relative FMC positions to be determined. As shown in FIG. 7A, when the FMC is shifted to a new location within the organ, the PME on the FMC measure a new set of signals (e.g., a new set of potentials). Based on the newly measured set of signals at the new location, a second local field model is constructed as shown in FIG. 7B. For illustration, the fields generated by source electrode #1 are shown in FIGS. 7A and 7B. Additional fields would be measured and additional local field models can be constructed based on the signals measured from the fields produced by the other current injecting electrodes.

The relative location of the FMC can be determined based on the local field models generated at each of the locations. To locate the second FMC position relative to the initial position, the system initially assumes that it occupies a particular, but likely incorrect, location. When the predictions of the two local field models on the regions of overlap are compared, the error in position will result in discrepancies between the predictions. For example, as shown in FIG. 7C, an initial position is assumed for the second location of the FMC. However, the field model generated for the second location does not match the previous model of the field so the FMC is assumed to be in the wrong location and orientation. This schematically shows how the second field model, which is tied to the coordinate frame of the FMC, does not match the previous model of the field when the FMC is assumed to be in the wrong location and orientation.

The system can determine the translation and orientation of the FMC at position #2 by minimizing the discrepancy between the models across all fields in the region of overlap. For example, as shown in FIG. 7D, the system determines the translation and orientation needed to align the two models. Schematically, this shows the perfect agreement between the two field models when the correct second position is chosen for the FMC.

Figure 8:
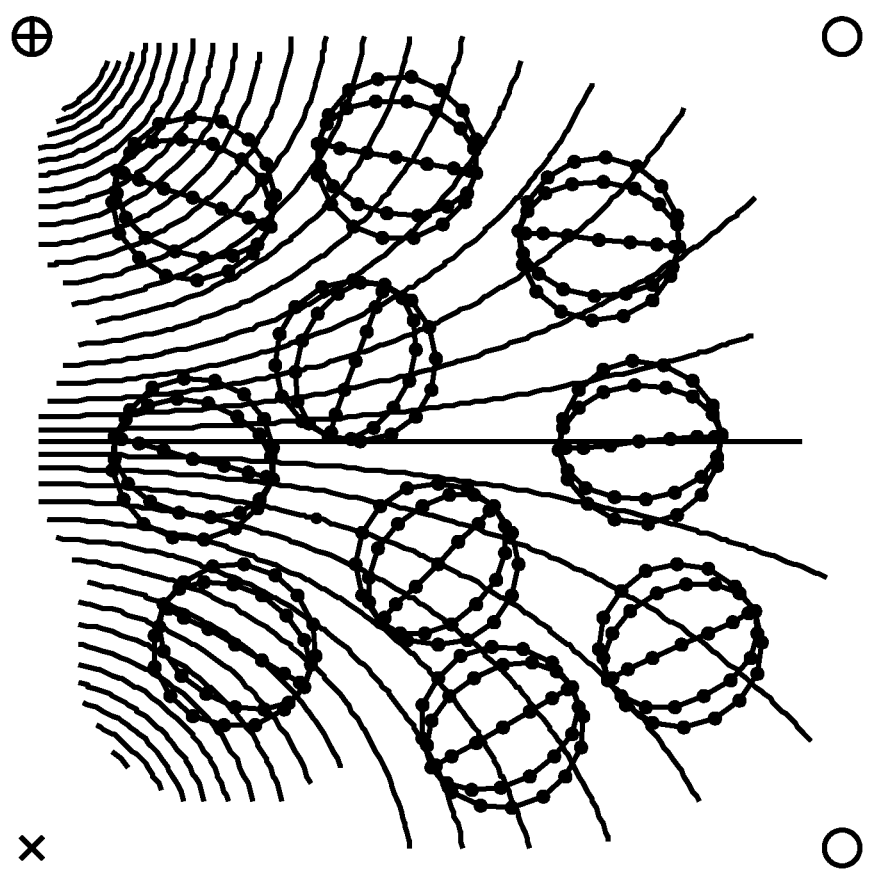
FIG. 8 is an exemplary field map.

As shown in FIG. 8, the system generates a combined field model based on modeled portions of the field (e.g., based on multiple local field models) by combining the multiple models to generate a combined field model. The system combines the multiple models based on the measured signals at each of the locations and the determined relative locations of the FMC at each of the locations. More particularly, the field mapping catheter is moved around inside the organ of interest while constantly measuring the generated fields (or while measuring fields at predefined time intervals or based on user selected times). The process of gathering signal measurements and aligning field models described above is repeated at several measurement locations. As shown in FIG. 8, the measurements from the multiple locations can be combined to generate a model of a larger portion of the field within the organ of interest. The signals measured at the multiple locations yields a set of measurements and relative positions that can be combined to provide a field description for the entire volume of interest.

The FMC measurements at the multiple locations are combined to create a field map for each CIE pair over the entire region of interest. This "global" field map is used for tracking individual electrodes or collections of electrodes. One method for generating the global field map is to predict the potential at a given location by using the local field generated by the nearest FMC measurement. This approach aligns and combines all of the individual local field models. A second method blends the local field models by weighted averaging depending upon the confidence in each local field model at the given location. A third approach is to generate a single field model using all of the FMC electrode measurements and locations (either concurrently or sequentially).

As more data are collected, the additional data can be used to improve the accuracy of the field map. The optimization used to find relative FMC positions can incorporate knowledge about the number and quality of the measurements that predict potentials in the area. The field map can be constructed, updated, and made more accurate as each new measurement becomes available. When the field map is considered sufficiently accurate, a new FMC measurement position (or a position of another measuring electrode on another catheter that is separate from the FMC catheter) can be determined by comparing the new measurements with the global field map rather than a subset of the previous measurements.

Local Field Model

The physical laws governing an exemplary method of reconstruction of the fields in the vicinity of the FMC are briefly summarized below. If the charge density at each point in a region of a homogeneous medium is zero, then the potential field satisfies Laplace's equation as shown in Equation1 1.

$$\vec{\nabla}^2 \phi = 0 \qquad (1)$$

A field satisfying Laplace's equation over a volume is completely determined by the potential on a surface enclosing the volume. Furthermore, Laplace's equation is linear, so the potential at any point within the volume is a linear combination (a weighted integral) of the surface potentials.

The surface potential can generally be approximated using a finite set of discrete elements such that each element represents the potential on a small region of the surface. Using this approximation, the potential at any point in the volume becomes a weighted sum of these surface potentials. Therefore, the potential at any set of points in the volume can be represented by a matrix multiplication with the surface potentials, as shown in Equation 22.

$$A\phi_s = \phi_v \qquad (2)$$

Equation 22 states that a set of volume potentials, $\phi_v$, are each calculated as a linear combination of the finite set of surface potentials, $\phi_s$. The elements of the matrix A can be determined by various methods such as finite element method, finite difference method, boundary element method etc. The matrix A depends on the surface elements as well as the volume locations at which the potential is to be calculated.

Figure 9:
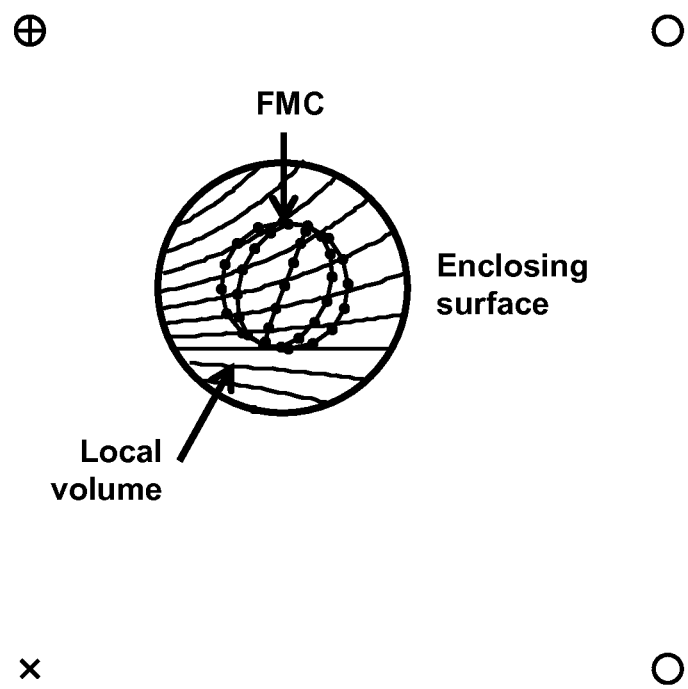
FIG. 9 is a diagram of an exemplary volume and an enclosing surface surrounding a field mapping catheter.
Figure 10:
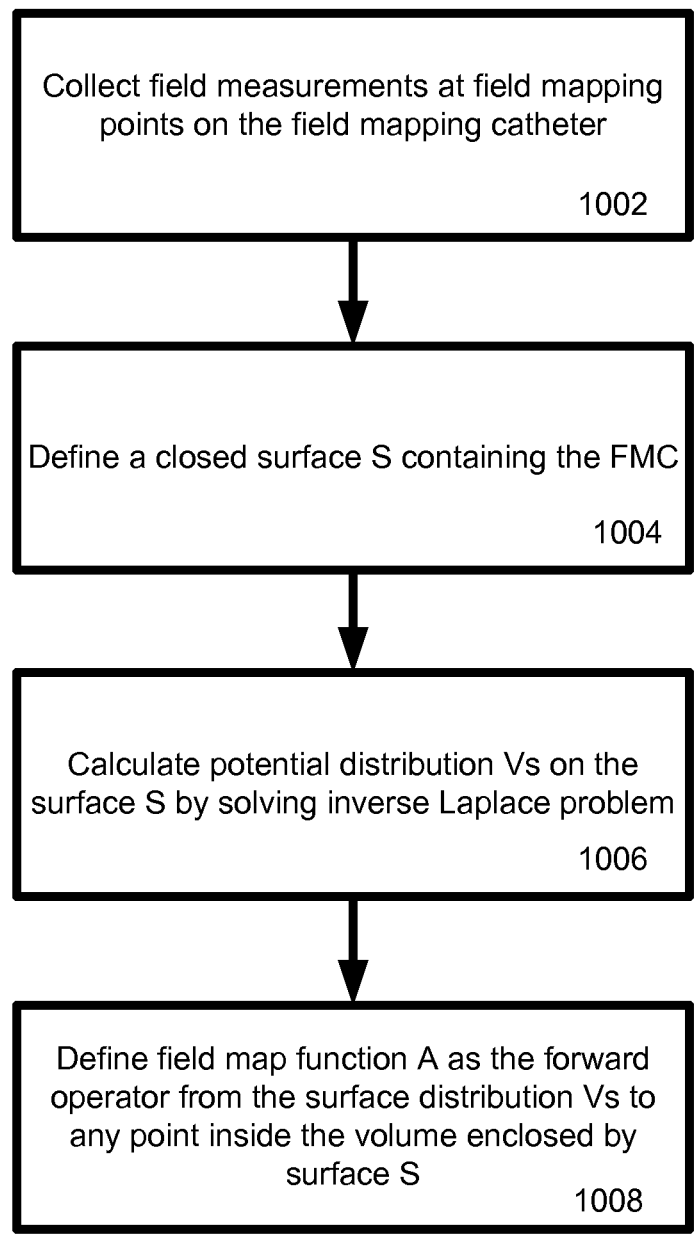
FIG. 10 is a flow chart of a method for generating a field map for an enclosed volume.

FIG. 10 shows a flow chart of a method for generating a field map for an enclosed volume. At step 1002, the system collects field measurements at field mapping points using the field mapping catheter. For example, as described above, the FMC can be moved to different positions within the organ and signals can be measured at each of the different positions. For a particular position (and associated set of signal measurements), at step 1004 the system defines a volume and an enclosing surface that surround the FMC. An exemplary volume and an enclosing surface surrounding the FMC is shown, for example, in FIG. 9. At step 1006, the system estimates the surface potentials (e.g., a potential distribution Vs on the surface S), and therefore all of the enclosed volume potentials, by solving Equation2 2 for the surface potentials with the FMC electrode measurements as the given volume potentials. Determining the estimated surface potentials can include solving an inverse Laplace problem. Therefore, the FMC electrode locations and the enclosing surface are used to find the values in the matrix A, and the measured electrode potentials are used for the volume potentials $\phi_v$.

In order to accurately represent the surface potential, the number of surface elements in $\phi_s$ tends to vastly exceed the number of FMC electrode measurements in $\phi_v$. As a result, the problem is underdetermined, implying that it has an infinite number of solutions. A unique solution can be found by solving a least-squares problem that includes a term constraining the surface potentials, as shown in Equation 33.

$$\hat{\varphi}_s = \underset{\varphi_s}{\mathrm{argmin}}(\|A\varphi_s - \varphi_v\|^2 + \alpha^2 \|L\varphi_s\|^2) \qquad (3)$$

There are two terms in this minimization. The first represents the squared approximation error in satisfying Equation 22, which should ideally be comparable with the expected measurement error. The second term represents the energy of a linear function of the surface potentials, and it is referred to as the regularization term.

If the matrix L in Equation 33 is diagonal, then the regularization represents a weighted sum of the squared surface potentials, so the minimization balances the approximation error against the solution energy. Another option is to use a matrix L such that $L\phi_s$ represents a weighted gradient of the surface potential. In that case, the minimization balances the approximation error against the variation of the potential across the surface. In either case, the regularization factor $\alpha$ controls the balance between the two error terms. The latter regularization scheme has been found to yield solutions that are smooth and yet accurate for a range of different regularization factors $\alpha$. A regularization factor of 0.01 is generally effective. Examples of the use of Equation 33, as well as further details regarding the matrix calculations, are described in patent application Ser. No. 11/451,898, entitled "NON-CONTACT CARDIAC MAPPING, INCLUDING MOVING CATHETER AND MULTI-BEAT INTEGRATION" and filed Jun. 13, 2006, the contents of which are incorporated by reference herein.

At step 1008, the system defines a field map function A as the forward operator from the surface distribution Vs to any point inside the volume enclosed by surface S. More particularly, after calculating the surface potentials using Equation 33, it is possible to calculate the potential at any point in the volume by applying Equation 22 for the given location (the matrix A depends on the point being calculated). This process of estimating the surface potentials and then calculating volume potentials is repeated for each generated field. This method generates a field map that is accurate for the entire enclosed volume.

It should be appreciated that similar methods can be used for generating field maps for different kinds of scalar or vector fields. An impedance field can be generated using the same inverse approach to achieve an accurate and differentiable impedance field map without interpolation. In the case where there are electrodes injecting currents inside the volume, such as the case in which the field mapping catheter is involved in the current injection, a similar inverse method can be used: instead of using Laplace's equation, a more general representation of the potential field, Poisson's equation, is used. Similar tools can be used for solving the inverse Poisson problem and generating a field map.

FMC Position Alignment

As described above, FMC measurements at the multiple locations (local field maps) are combined to create a field map over the entire region of interest. This "global" field map is used for tracking individual electrodes or collections of electrodes. In order to generate the global field map, the system determines relative positions of the FMC for different signal measurements and combines multiple individual local field models using the determined relative positions.

More particularly, in order to determine the relative positions of the FMC, the system solves an optimization problem to find the rotation and translation of a new FMC measurement relative to an existing field map.

Suppose that $\phi_i(r)$ is the existing model of the $i^{th}$ field at the location r in the coordinate system of the field map. A new measurement with the FMC provides an estimate of the fields at a discrete set of points in the region around the FMC, and these estimates are denoted $\psi_{ij}$ for the $i^{th}$ field and the $j^{th}$ point. The locations of these field estimates are specified relative to the FMC itself rather than the existing field map, and they are denoted $p_j$. The corresponding points in the coordinate system of the field map depend on the rotation $\theta$ and translation t of the FMC and are denoted $r_j(\theta, t)$. The field estimates $\psi_{ij}$ for the new measurement are therefore expected to match the field map values $\phi_i(r_j(\theta, t))$ when the orientation $\theta$ and translation t are chosen correctly. We can solve for these parameters by minimizing a sum of squared errors as shown in Equation 4 below.

$$(\hat{\theta}, \hat{t}) = \underset{(\theta,t)}{\mathrm{argmin}} \sum_i \sum_j w_{ij} |\varphi_i(r_j(\theta, t)) - \psi_{ij}|^2 \qquad (4)$$

The sum of squared errors penalizes for differences in the field predictions over a discrete set of points in the vicinity of the FMC. It weights the penalty for the error at the $j^{th}$ point in the $i^{th}$ field by a weight $w_{ij}$. These weights incorporate a priori and a posteriori knowledge of the measurement error, modeling error, and region of valid overlap. For example, the modeling error is sensitive to distance from PMEs, so the weights may incorporate a term that is inversely proportional to the distance to the nearest electrode in the FMC. Any standard nonlinear optimization technique can be used to solve Equation 4 for the optimal parameters $(\hat{\theta}, \hat{t})$.

An alternative method for determining the relative positions of a set of measurements is to create a common field model that predicts the field in a volume encompassing all of the measurements. For example, the common field can be modeled using the finite element method. The error between the model and the measurements is then minimized to find the rotation and translation of each FMC position. In this case, the model $\phi_i$ of the $i^{th}$ field depends on all of the assumed FMC electrode locations and measured potentials, as shown below in Equation 5.

$$\phi_i(r) = \phi_i(r | \{r_i(\theta_k, t_k) \forall j, k\}, \{\psi_{ijk} \forall j, k\}) \qquad (5)$$

Here, the new subscript k has been introduced to index each separate FMC measurement and position. Equation 5 shows that the field model at position r depends on all of the FMC electrode locations and all of the measured potentials.

If the $k^{th}$ FMC measurement of the $j^{th}$ electrode in the $i^{th}$ field is denoted $\psi_{ijk}$, and if the FMC electrode locations for the $k^{th}$ measurement are denoted $r_i(\theta_k, t_k)$ in the coordinate system of the field model, then the measurement positions can be found by minimizing a sum of squared errors as shown in Equation 6 below.

$$(\hat{\theta}_1, \hat{t}_1, \ldots, \hat{\theta}_k, \hat{t}_k) = \arg\min_{(\theta_1, t_1 \ldots, \theta_k, t_k)} \sum_i \sum_j \sum_k |\varphi_i(r_j(\theta_k, t_k)) - \psi_{ijk}|^2 \quad (6)$$

This minimization is similar to Equation 4 except for the additional measurements and the model dependency on all of the positions and measurements. It should be noted that the overall translation and rotation of the field model is arbitrary. This is resolved in Equation 7 by omitting from the minimization $\theta_0$ and $t_0$, the positional parameters of the first FMC measurement. These are assumed to be fixed, and they define the coordinate system of the field model. It should also be noted that Equation 8 can be modified to include weights as in Equation 4, and they can vary across field, electrode, and measurement.

Global Field Map Generation

The system can use various methods to generate the local field maps. One exemplary way to generate either a local field model or a global field map is to generate a 3D grid with a resolution that fits the required accuracy of the tracking system and then apply interpolation techniques to the measured values. For example, the grid resolution may be 0.2 mm. An interpolation algorithm such as cubic interpolation can be used to interpolate the measured values onto the grid.

An alternative method of generating the field model merges the local field model from each successive FMC position into a continually improving global field map on a grid spread throughout the volume of interest. Each local field model can be oriented with respect to the grid on the region of interest, and it will provide predictions of the field on the grid points contained within the local volume. The existing global field map values on the grid points have weights associated with them, approximately representing the confidence attached to the field map at each point. Similarly, the local volume predictions will have compatible weights. The existing field map and the new local model can be combined at each grid point using these weights, e.g., by using a simple weighted mean of the estimates as shown below in Equation 9.

$$\varphi(r) = \frac{1}{w(r) + w_{local}(r)}(w(r)\varphi(r) + w_{local}(r)\varphi_{local}(r)) \quad (9)$$

In Equation 9, $\varphi(r)$ is the field map at the grid point r, $\varphi_{local}(r)$ is the new local estimate of the field at the same point based on a new FMC measurement, w(r) is the weight associated with the existing field map at r, and $w_{local}(r)$ is the weight associated with the new local estimate at that point. The field map $\varphi(r)$ is replaced with the weighted mean of the existing and new values. The weight w(r) must also be updated to reflect the new information. One method for updating the weights is to simply add the new and old weights as shown in Equation 10.

$$w(r) = w(r) + w_{local}(r) \quad (10)$$

The weights in this method can be taken to represent the inverse error variance of the field estimate at each point. For the local field model, the inverse error variance can be estimated using the local modeling error and the expected error trends across the local volume, such that the error is assumed to be low near the PME electrodes and when the measured potentials closely match the local model. The inverse error variance at the grid points of the field map can be initialized to zero (this assumes infinite initial error). It should be noted that this process of updating the field model and, weight must be repeated for each field (each CIE configuration).

Tracking

Once a set of expected signal measurements (e.g., a field map) has been constructed representing a region of interest, the field map can be used to track electrodes and catheters within that region. The tracked electrodes can be potential measuring electrodes on the FMC catheter and/or other potential measuring electrodes on different catheters. Using the field map, multiple electrodes (on one catheter or on multiple, different catheters) can be tracked simultaneously.

PME tracking, which is described in more details below, is accomplished by comparing PME measurements with expected signal measurements (e.g., the measurements predicted by the field map) and then choosing the PME location that provides the best match. Catheter tracking, which is also described in more detail below, is accomplished similarly except that PME locations are forced conform to the expected shape of the catheter on which they reside, or alternatively, the optimizer is penalized for deviations from the expected shape constraints. PME and catheter tracking can be degraded by variations in field measurements with cardiac and respiratory cycle. Methods compensating for these variations (e.g., the variations due to cardiac and respiratory cycles) are also described below.

PME Tracking

Tracking of PME is performed by solving an optimization problem that compares the measurement collected by the PME as a result of activation of the DIE pairs to expected measurements in the field map in a given location. The electrode is assigned the location that in some way minimizes the error between the expected field in the field map and the measured field. The following describes one exemplary method for determining the location of the tracked PME. However, other methods are possible.

Figure 11:
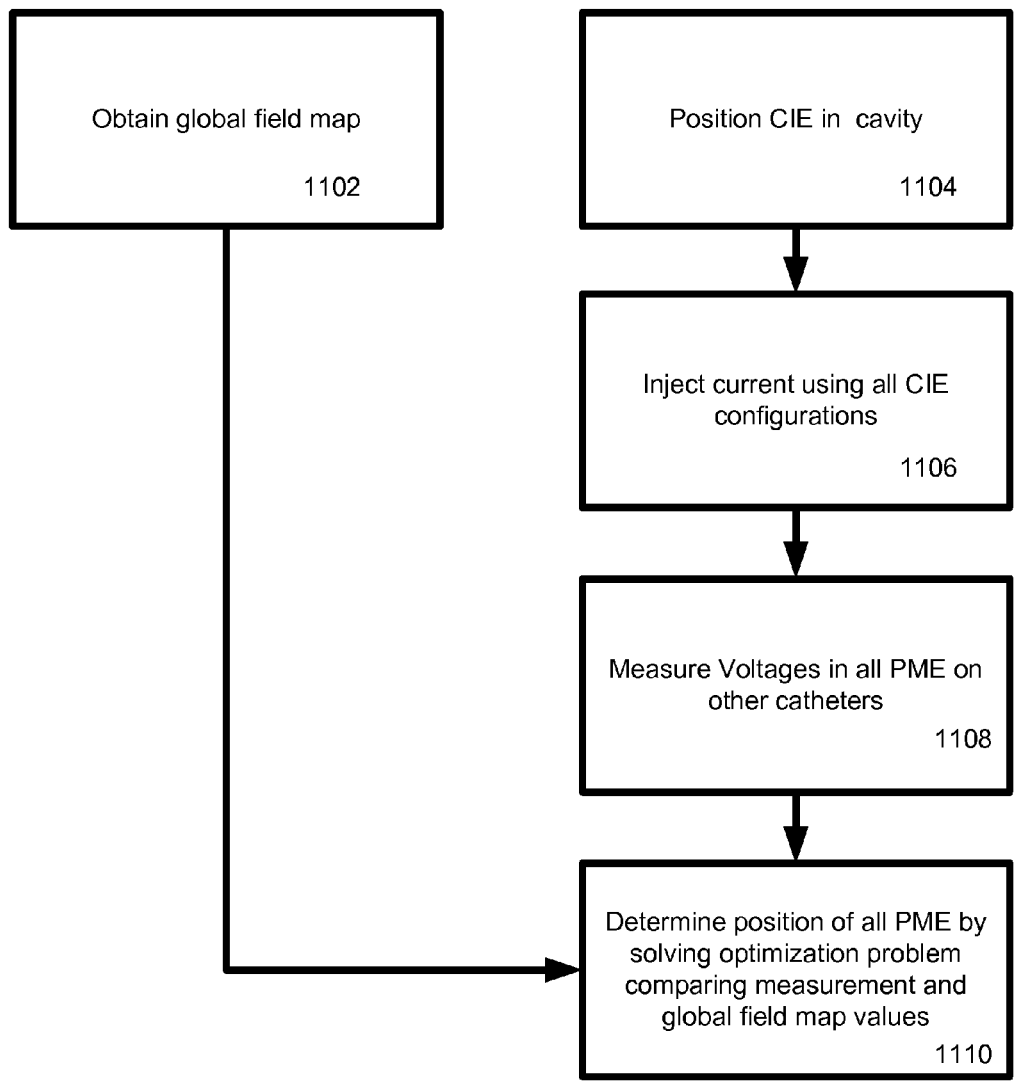
FIG. 11 is an exemplary flow chart for determining positions of electrodes using a field map.

FIG. 11 shows an exemplary flow chart of a process for determining positions of PME using a field map (e.g., a field map generated using one or more of the methods described herein).

At step 1102, the system obtains a field map. The field map assigns field measurements to each location in space and can be generated using one or more of the methods described herein.

At step 1104, CIE are positioned in the cavity (these CIE are the same CIE used to generate the field map). At step 1106, the system causes the CIE to inject current using each of the CIE configurations used to generate the field map. For example, in the case of three CIE pairs, each location in 3D space r=(x,y,z) is assigned three measurements, $\phi_1(r)$, $\phi_2(r)$, and $\phi_3(r)$, corresponding to the three different fields generated by the CIE pairs. At step 1108, signals are measured on the PME on catheters positioned in the organ (e.g., the tracked catheters). In the example with three CIE pairs, three measured potentials, $v_1$, $v_2$, and $v_3$, are obtained from the tracked PME: one for each CIE pair. Based on the measured signals and the field map, at step 1110, the system determines positions for each of the PME by solving an optimization problem that compares the measured signals with the values of the expected signals in the field map. Accordingly, the PME can be assigned the location, $\hat{r}=(\hat{x},\hat{y},\hat{z})$, that minimizes the sum of squared measurement errors as shown in Equation 11.

$$\hat{r} = \arg\min_r \sum_i |\varphi_i(r) - v_i|^2 \quad (11)$$

Equation 11 is a nonlinear optimization problem, and it can be solved using an iterative scheme such as Newton-Raphson or Levenberg-Marquardt or a direct search method such as the Nelder-Mead Simplex Method. The optimization in Equation 11 determines the location of PME without any prior knowledge of the CIE spatial configuration or any prior knowledge of the characteristics of the medium. In the case of more than three pairs of CIEs, the solution for $\hat{r}$ becomes over-determined since we obtain more equations than unknowns, which may help improve tracking accuracy depending on the specific embodiment.

The optimization in Equation 11 can be modified in several ways to adjust the behavior of the tracking algorithm. A weighting factor can be applied to the error in each field, which can be used, for example, to prevent the solution being dominated by the contribution of the nearest CIE. The sensitivity of the optimization to each field error can also be adjusted by replacing the sum of squares with a sum of errors raised to a different power; for example, raising error to the fourth power makes the optimization more sensitive to the largest error among the fields, whereas summing the absolute value of each error makes the optimization less sensitive to the worst field error. Another option is to use a sorting filter, such as a weighted median or maximum, in place of the sum of squares. Using a sorting filter also adjusts the sensitivity of the optimization to outlying errors.

It should be appreciated that more than one PME may be tracked simultaneously using this scheme. To do so, signals are acquired from and an optimization problem is solved for each of the electrodes being tracked. If such electrodes are mounted on different catheters, then it is possible to simultaneously track multiple catheters.

The measurements collected at the PMEs as a result of current injected by the CIE are generally affected by the complex conductivity, or admittivity, distribution of the medium. It should be noted that the optimization in Equation 11 is valid for either real- or complex-valued measurements. As a result, both amplitude and phase may be used for tracking purposes. Use of the imaginary part of the complex conductivity is of particular importance in material distributions where the permittivity contrast exceeds that of the conductivity contrast.

Catheter Tracking

By tracking the individual PME on a catheter, the location and shape of the catheter can be determined. Also, because measurements from multiple PME are used to track the catheter, tracking accuracy can be improved over what is possible with a single PME. PME can be constrained by the catheter in several ways as described below.

If the electrodes are constrained in such a way that they cannot move relative to each other, then the catheter is considered a rigid body, and only the translation and rotation of this body must be determined by optimization. The catheter position can be found by minimizing a sum of squared errors as in Equation 11 except that (1) the errors are summed over all PME and (2) the PME locations are determined by translating and rotating a set of reference locations representing the positions of the PME on the catheter. The optimization then finds the catheter translation and rotation that minimize the error over all PME, and this gives the position of the region of the catheter where the PME are located. (The shape of the catheter is fixed and known.) As in the case of individual PME, the optimization in Equation 11 can be modified by weighting the errors from each field and each PME or by replacing the sum of squared errors with a different, possibly nonlinear, combination of errors.

If the electrodes are constrained such that their spacing cannot change, then inverse kinematics can be used to solve for their positions. Inverse kinematics solves for the joint angles of a chain of joints connected by rigid segments. As before, some combination of errors over all fields and all PME can be minimized to find the PME locations, but at each step in the optimization, the locations of the PME are constrained to maintain the segment lengths. The optimization finds the position of each PME, giving the shape and position of the region of the catheter where the PME are located. The kinematic model assumes that the catheter forms a straight line segment between each pair of PME, but interpolation methods can be applied in order to find a more realistic shape for the catheter.

The PME tracking problem in Equation 11 can be augmented with penalties for incorrect catheter shape. For example, a second error term can be added to Equation 11 that quantifies the difference between the predicted electrode spacing and the expected spacing. By adjusting the relative weight applied to this second error term, the balance between measurement error and spacing error can be adjusted in the optimization. As another example, the PME can be taken to lie on a flexible beam, and the predicted beam stress or loading can be used as an additional error term in Equation 11. These methods do not directly result in a shape for the catheter, but interpolation methods can be used to solve for the complete catheter shape.

Another exemplary method for tracking a catheter is to solve for the locations of each of the PME and then fit them onto a model of the catheter. For example, if the catheter is taken to be a rigid body, then the catheter translation and rotation can be found that minimize the distance between the PME on the rigid body and the optimized PME locations. As another example, the shape of a kinematic chain can be found such that the distance between the joints and the optimized PME locations is minimized.

Cardiac and Respiratory Motion

Cardiac contraction and respiration change the medium in which the fields are being generated, thus changing the generated fields. In other words, the actual fields are time-varying. There are several ways to address this issue.

One approach is to apply a low-pass filter to the measured potentials in order to reduce measurement variation due to cardiac and respiratory cycles. For example, a filter that only passes signals below the fundamental frequency of the respiratory and cardiac cycles will remove their effects.

A second approach is to generate separate field maps for various phases in the cardiac and respiratory cycle: this is called phase-gating. In this case, a PME is tracked by optimizing its location in a field map corresponding to the current cardiac and/or respiratory cycle phase. The cycle phase is detected using measurements from PME on stationary catheters, such as those on which the CIE reside, and/or cutaneous patches such as ECG. The variation in these stationary measurements is due to cardiac and respiratory cycle. By comparing the current stationary PME measurements with previous measurements corresponding to each phase, the current phase can be determined. Templates or exemplars for each phase can be picked by various clustering methods such as, for example, k-means clustering.

A third approach is to normalize the data for the field variation due to cardiac and respiratory cycle. A substantial part of the field variation is additive and is common to all measurements in the region of interest. It is possible to synthesize this additive component using measurements from a set of PME on stationary catheters (e.g. where the CIE reside)

and then subtract it from the measured potentials. The additive phase variation is thereby removed from the measurements.

The additive phase-dependent field variation can be synthesized as follows. When the FMC is in a stationary position, the variation in its measurements is largely due to cardiac and respiratory cycle. With the FMC in a stationary position in the region of interest, the mean measurement across the electrodes on the FMC (the FMC common mode) is calculated, and then the mean across time is subtracted from it. The resulting signal represents the expected phase-dependent field variation for FMC measurements in the region of interest. This variation can be approximately synthesized as a linear combination of the PME measurements on stationary catheters. The mean across time is subtracted from each stationary PME measurement, and the result represents the phase-dependent field variation detected by each stationary PME. The linear combination of PME measurements is selected such that the combination of PME phase-dependent field variations best matches the phase-dependent field variation measured by the FMC.

One specific method for determining the desired linear combination of stationary PME measurements is described below. As shown in Equation 12, a linear least-squares problem can be solved to find the weights that should be applied to the stationary PME measurements such that their sum best approximates the expected phase-dependent field variation on the FMC.

$$\phi_{CM} - E\{\phi_{CM}\} = [\phi_{S1} - E\{\phi_{S1}\} \phi_{S2} - E\{\phi_{S2}\} \ldots ] \cdot \alpha \quad (12)$$

In the above: $\phi_{CM}$ is the mean across the FMC electrodes (common mode); $E\{\bullet\}$ is the mean over time; $\phi_{S1}$ is the measurement from the first stationary PME; and $\alpha$ is the set of weights applied to each stationary PME measurement. This linear equation is solved for the weights $\alpha$ using least squares, and the resulting weights are used to synthesize the additive phase variation component. The above procedure must be repeated for each field.

There are several related ways to solve for the set of weights applied to the stationary PME measurements in order to synthesize the additive phase-dependent field variation. Rather than only solving using measurements in one stationary FMC position, the weights can be found that optimize for multiple stationary FMC positions by vertically concatenating the corresponding measurements in Equation 12 and solving for a single set of weights. Also, rather than solving a linear least-squares problem for the weights, a more general optimization approach can be used to solve for the weights. For example, standard optimization techniques can be used to find weights that are nonnegative or that sum to 1.

An additive correction for phase-dependent field variation only compensates for an overall offset in the field, but it is possible to compensate for higher-order variations in each field due to cardiac and respiratory cycle. For example, a phase-dependent scaling term can be used to compensate for changes in field strength with cardiac and respiratory cycle. Such a scaling term can be determined by collecting FMC measurements in a set of stationary locations and then optimizing for a combination of stationary PME measurements that best approximates the phase-dependent field strength variation.

FGD Displacement Correction

As described above, PME are tracked based on a comparison between a set of expected signals (e.g., a field map) and a signal measured on a PME of a tracked electrode where the CIE used to generate the signals for obtaining the field map and for tracking the PME are the same (and are in the same locations). In order to correctly determine the position of tracked electrodes, the CIE should be kept in the same location as they were in when the field map was generated. However, during field mapping or catheter tracking, the FGD may become unintentionally displaced. For example, if several CIE reside on a catheter in the coronary sinus, a catheter moving in the right atrium may come into contact with the coronary sinus catheter and displace it. The catheter carrying the FGD may also be displaced due to patient respiration or other patient movement. One approach to overcoming this issue is the use of a device or method to keep the FGD carrying catheter stably positioned. This can be accomplished by using any of a number of fixation schemes, for example scaffolding or a balloon anchor. Another approach is a subsystem that can detect such displacement and aid the user in correcting it. This can be accomplished in several ways as described below.

FGD displacement correction involves the detection of relative displacement between FGD and one or more PME that are known to be in a stable position. Cutaneous PME or stable intracardiac PME can be used to collect stable measurements for this purpose. In particular, standard ECG leads, which are PME, can be used for the dual purpose of measuring cardiac electrical activity and monitoring tracking signals using the multiplexing scheme described earlier. Furthermore, additional cutaneous PME can be used to increase the accuracy of the displacement correction subsystem.

With the FGD in an initial position, stable PME can be used to form a baseline measurement of the generated fields (for example, the system can cause current to flow among the current injecting electrodes and measure signals at measuring electrodes positioned at one or more secure locations). Measurements from the stable PME (e.g., signals measured at the PME in response to current flow from the current injection electrodes) are then monitored and compared to the baseline measurements to detect changes due to displacement of the FDG. The error between the baseline and the current measurements can be quantified using a distance metric, such as the L2 norm, and displacement can then be detected by comparing the error metric with a threshold value. If the error metric exceeds the preset threshold, the clinician is alerted that the FGD has been displaced.

In addition to alerting the clinician, the error metric can be used to guide the catheter back to the initial position. As the clinician moves the displaced FGD, the value of the error metric is displayed and updated. When the error metric falls under the preset threshold, an indication is provided that the FGD has returned to the initial position.

Furthermore, the signals collected by the stable PME can be used to guide the catheter back to the initial position by approximately tracking the FGD in 3D space. FGD tracking can be accomplished in a number of ways, several of which are outlined below.

As in the case of PME tracking, FGD tracking requires a model of the generated fields—the equivalent of a field map. The fields generated by the FGD are modeled in the vicinity of the stable PME. PME measurements can be tracked in this field model to determine the displacement of the generated fields and thus the displacement of the FGD. Inaccuracies in the field model will cause the detected displacement to be distorted, but it can still provide useful information to the clinician or to the tracking algorithm.

For example, a three-dimensional polynomial model can be fit to the initial measured data if the approximate locations of the stable PME are known. It is then assumed that the field model moves with the FGD, and therefore any change in the stable PME measurements relative to the field model is indicative of FGD movement. Displacement of the FGD can therefore be quantified by tracking the PME measurements as a rigid body within the field model using rigid body catheter tracking techniques described in the previous section.

Rather than modeling the field in the vicinity of the stable PME using the initial measurements and then tracking subsequent PME measurements within this model, other approaches can be used to determine the FGD displacement. For example, a field model can be constructed for each measurement, and then the rigid body motion can be determined that provides the best match between the two models in the region of the PME. As another example, a single field model can be constructed that best matches both the initial measurement and the current measurement such that the two measurements are related by a rigid body motion.

Other mathematical methods can be used to model the fields for FGD tracking. For example, rather than modeling each field as a polynomial, the CIE generating each field can be modeled as electric monopoles in a homogeneous medium. Given a set of stable PME measurements and their approximate locations, the monopole locations (and thus CIE locations) and monopole strengths can be determined that best match the measured potentials. This field modeling approach is similar to the polynomial field modeling approach, but it has the benefit that each field model defines the CIE locations, whereas the polynomial field model only gives the relative displacement of the entire field. As before, inaccuracies in the field model will distort the tracked FGD locations, but the tracked positions can still provide useful information to the clinician.

If the stable PME locations are unknown but the initial CIE locations are known, for example, based on the field map constructed for PME tracking, an electric monopole model can be used to determine the locations of the stable PME measurements, and subsequent stable PME measurements can be used to track displacement of the CIE. In this way, all of the spatial information required for both PME tracking and FGD tracking can be derived from the shape of the FMC and the measurements collected from the available PME.

When different fields are generated by some of the same CIE, or when different CIE on the same FGD are used, FGD tracking can be constrained using this information. For example, if each field is generated by a different CIE on the same FGD, and if each CIE is modeled as an electric monopole as described above, the optimization used to find the monopole locations can be constrained such that the monopoles obey known inter-electrode spacing on the shared FGD. This will yield more a more realistic FGD shape and can make the FGD tracking more robust. Other catheter shape constraints, such as a rigid catheter shape, can be used to improve CIE and FGD tracking.

Cardiac and respiratory motion will cause the FGD to move relative to the fixed PME and will also distort the PME measurements. This phase-dependent measurement variation can be compensated using the methods described in the previous section for compensating tracked PME measurements.

Experimental Results

Field mapping, electrode tracking, and FGD tracking have been demonstrated ex vivo using measurements collected in a nine-liter saline tank. The field mapping and electrode tracking results reported below were collected using two commercially-available decapolar catheters as FGD, a multielectrode array catheter as described in application Ser. No. 12/005,975 as the FMC, and a commercially-available decapolar catheter as the tracked catheter.

Figure 12:
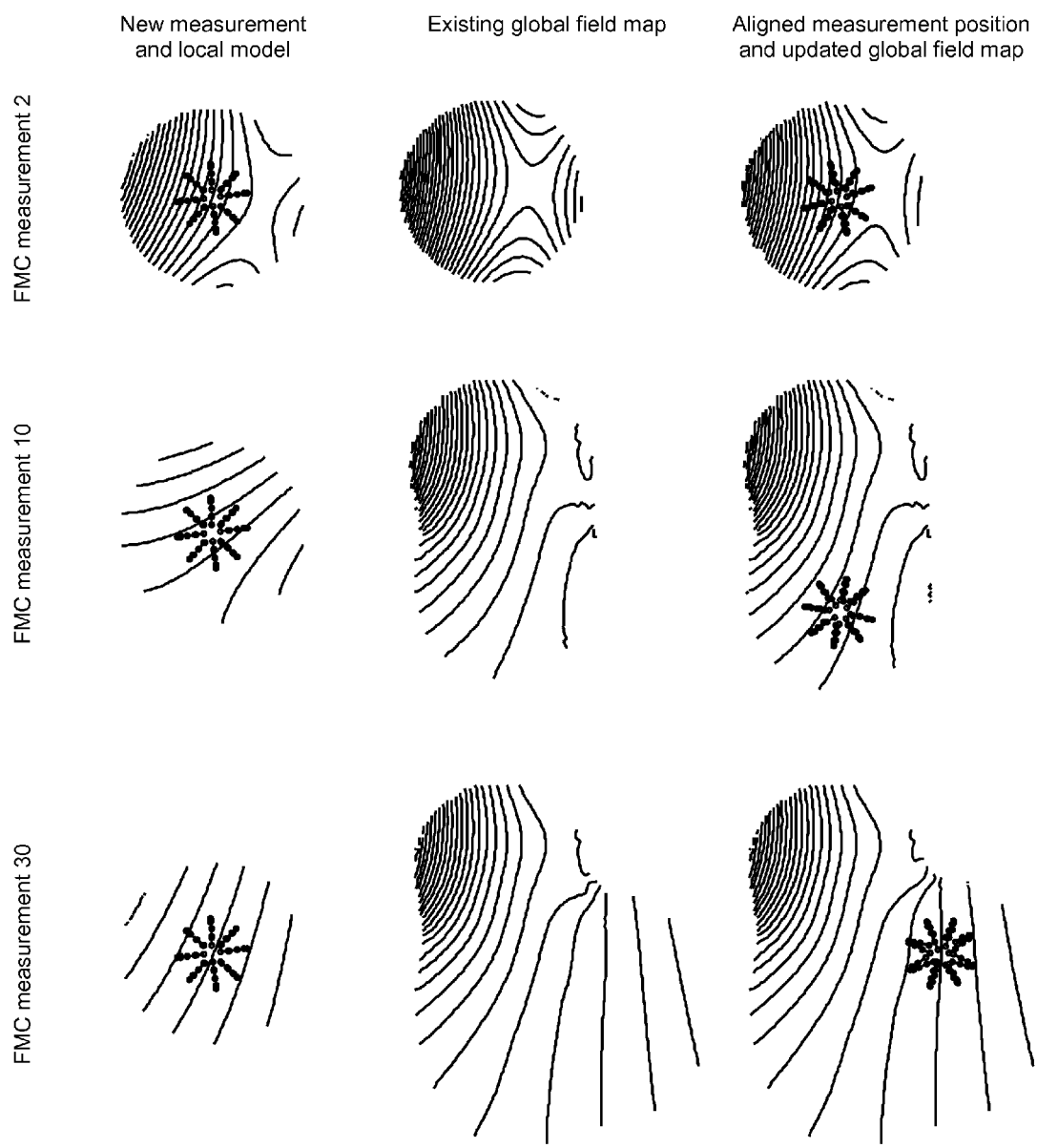
FIG. 12 is a table that includes contour plots of two-dimensional slices of the local model and global field map.

FIG. 12 shows a table of experimental results. The table includes contour plots of two-dimensional slices of the local model and global field map as new measurements are aligned and combined with the existing field map for one field.

In the experimental results shown in FIG. 12, the FMC was manually moved within the saline, and the FMC measurements collected in eight fields were used to construct a global field map using the methods described above in Equations 4, 9, and 10. Contour plots of two-dimensional slices of one of the eight fields of the local model and the global field map are used in FIG. 12 to show how each is generated with sequential FMC measurements. Each row shows the new local model, the existing global field map, and the updated field map for a new FMC measurement. In the first column, the FMC electrodes are shown superimposed on the local model generated from the new measurement. In the third column, the positions of the FMC electrodes after alignment are shown superimposed on the new global field map following the update. Each new local model slightly modifies and expands the global field map in the region around the FMC.

Figure 13:
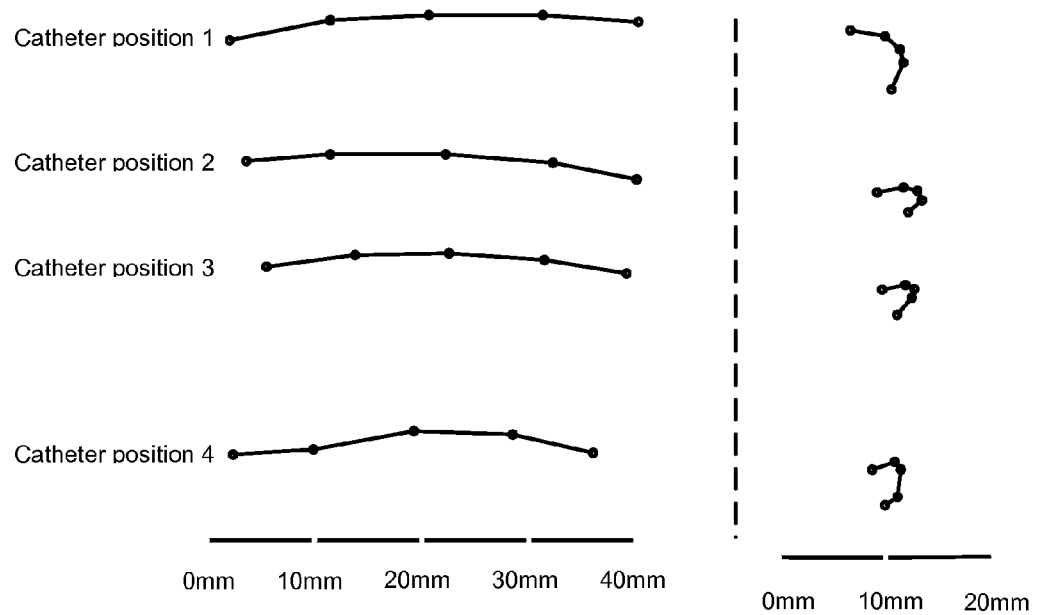
FIG. 13 is a diagram of three-dimensional tracked PME locations.

The field map constructed as shown in FIG. 12 was used to track PME on a commercially-available decapolar catheter using potential measurements collected from the PME in the saline tank with the tracking method described in Equation 11. Three-dimensional tracked PME locations are shown from two views in FIG. 13 for four different catheter positions. For clarity, tracked locations for only five of the PME are plotted, and they are connected with lines to show the shape of the decapolar catheter. The physical spacing between the tracked PME is 9 mm, so the total length of the tracked section of the catheter is 36 mm.

Other Embodiments

The methods and systems described herein are not limited to a particular hardware or software configuration, and may find applicability in many computing or processing environments. The methods and systems can be implemented in hardware, or a combination of hardware and software, and/or can be implemented from commercially available modules applications and devices. Where the implementation of the systems and methods described herein is at least partly based on use of microprocessors, the methods and systems can be implemented in one or more computer programs, where a computer program can be understood to include one or more processor executable instructions. The computer program(s) can execute on one or more programmable processors, and can be stored on one or more storage medium readable by the processor (including volatile and non-volatile memory and/or storage elements), one or more input devices, and/or one or more output devices. The processor thus can access one or more input devices to obtain input data, and can access one or more output devices to communicate output data. The input and/or output devices can include one or more of the following: Random Access Memory (RAM), Redundant Array of Independent Disks (RAID), floppy drive, CD, DVD, magnetic disk, internal hard drive, external hard drive, memory stick, or other storage device capable of being accessed by a processor as provided herein, where such aforementioned examples are not exhaustive, and are for illustration and not limitation.

The computer program(s) can be implemented using one or more high level procedural or object-oriented programming languages to communicate with a computer system; however, the program(s) can be implemented in assembly or machine language, if desired. The language can be compiled or interpreted. The device(s) or computer systems that integrate with the processor(s) can include, for example, a personal computer(s), workstation (e.g., Sun, HP), personal digital assistant (PDA), handheld device such as cellular telephone, laptop, handheld, or another device capable of being integrated with a processor(s) that can operate as provided herein. Accordingly, the devices provided herein are not exhaustive and are provided for illustration and not limitation.

References to "a microprocessor" and "a processor", or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network using a variety of communications protocols, and unless otherwise specified, can be arranged to include a combination of external and internal memory devices, where such memory can be contiguous and/or partitioned based on the application. Accordingly, references to a database can be understood to include one or more memory associations, where such references can include commercially available database products (e.g., SQL, Informix, Oracle) and also proprietary databases, and may also include other structures for associating memory such as links, queues, graphs, trees, with such structures provided for illustration and not limitation.

Accordingly, other embodiments are within the scope of the following claims.

What is claimed is:

1. A method comprising:
causing current to flow among multiple current injecting electrodes, at least some of the current injecting electrodes being placed in stable locations relative to a patient's body to generate a field in an organ;
in response to the current flow caused by the current injecting electrodes placed in stable locations relative to the patient's body, measuring a signal at each of multiple measuring electrodes on a catheter for each of multiple locations of the catheter to generate information about fields measured at each of the multiple locations;
determining local field maps, wherein each of the local field maps is based on the measured signals for the catheter at a location corresponding to the local field map and characterized by a field function, of potential distribution on a closed surface around the location to points inside the closed surface, that is determined from the measured signals at the location;
subsequent to determining the local field maps, determining a combined model of a field that includes expected signals at additional locations within the organ based on the measured signals by:
reconciling the local field maps to determine relative locations of the local field maps; and
combining the local field maps to generate the combined model of the field; and
subsequent to determining the combined model of the field, determining a position of at least one electrode selected from the group consisting of at least one of the measuring electrodes of the catheter and a measuring electrode of another catheter in the organ based on at least measurements made by the at least one electrode and the combined model of the field that includes the expected signals.

2. The method of claim 1, wherein the current injecting electrodes are not on the catheter that includes the measuring electrodes.

3. The method of claim 1, wherein determining the expected signals comprises determining expected signals in the absence of information from an external tracking system.

4. The method of claim 1, wherein reconciling the local field maps comprises minimizing a cost function on one or more of a point, multiple points, a surface, and a volume.

5. The method of claim 1, wherein reconciling the local field maps to determine the relative locations comprises determining a translation and rotation between the measuring electrodes at the multiple locations.

6. The method of claim 1, wherein the combining comprises aligning information from different local field maps to account for different locations of the catheter based on known relative locations of the measuring electrodes on the catheter.

7. The method of claim 1, wherein determining the expected signals comprises reconciling the local field maps from the multiple locations.

8. The method of claim 7, wherein reconciling the local field maps comprises minimizing a cost function on one or more of a point, a surface, and a volume.

9. The method of claim 7, wherein reconciling the local field maps comprises determining a translation and rotation between the local field maps.

10. The method of claim 1, wherein determining the expected signals comprises determining the expected signals based on the measured signals and known relative locations between the multiple measuring electrodes on the catheter.

11. The method of claim 1, wherein the expected signals comprise a field map.

12. The method of claim 11, wherein the field map comprises a differentiable function.

13. The method of claim 1, wherein determining the expected signals comprises using Laplace's equation.

14. The method of claim 1, wherein determining the expected signals comprises using Poisson's equation.

15. The method of claim 1, wherein determining the expected signals comprises using a polynomial estimation.

16. The method of claim 1, wherein the current injecting electrodes are mounted on one or more catheters that are secured inside the organ.

17. The method of claim 1, wherein the current injecting electrodes comprise both electrodes mounted on one or more catheters secured inside the organ and one or more body-surface electrodes.

18. The method of claim 1, wherein measuring the signal comprises measuring potentials.

19. The method of claim 1, wherein measuring the signal at the multiple locations comprises moving the catheter to the multiple locations within the organ, and using the measuring electrodes to measure signals for each of the multiple locations of the catheter.

20. The method of claim 1, wherein combining the local field maps comprises sequentially combining the local field maps to generate the combined model of the field.

21. The method of claim 1, wherein combining the local field maps comprises concurrently combining the local field maps to generate the combined model of the field.

22. The method of claim 1, wherein the combined model of the field comprises a weighted mean of the local field maps.

23. The method of claim 1, further comprising:
removing the measuring electrodes from the organ; and
subsequent to removing the measuring electrodes from the organ using the expected signals to track a location of the measuring electrode of the another catheter.

24. The method of claim 1, wherein the current injecting electrodes comprise at least three sets of current injecting electrodes, and wherein the causing of the current flow comprises causing current to flow between each set of current injecting electrodes.

25. The method of claim 1, wherein the organ is the patient's heart.

26. The method of claim 1, wherein determining the position comprises determining the position of the measuring electrode of the another catheter with the another catheter being a separate catheter from the catheter that includes the multiple measuring electrodes.

27. The method of claim 1, wherein the measured signals and expected signals are processed to account for respiration and heart beat.

28. The method of claim 27, wherein processing the measured signals and expected signals comprises using information from a catheter electrode positioned in a stable location relative to the organ.

29. The method of claim 28, wherein the stable location comprises the coronary sinus.

30. A method comprising:
causing current to flow among current injecting electrodes that are placed in stable locations relative to a patient's body to generate fields in an organ;
measuring signals at measuring electrodes on a catheter for each of multiple locations of the catheter to generate information about the fields at the multiple locations;
generating expected signals at additional locations;
determining local field models, wherein determining a local field model at each location of the multiple locations comprises:
defining a closed surface containing the location;
calculating potential distribution on the closed surface; and
defining a field function from the potential distribution to points inside the closed surface; and
determining a combined field model comprising:
reconciling the local field models at the multiple locations to determine relative locations of the local field models; and
combining the local field models to generate the combined field model.

31. The method of claim 30, comprising:
determining a position of at least one measuring electrode based on one or more measurements made by the at least one measuring electrode and the combined field model.

32. The method of claim 30, wherein reconciling the local field models comprises:
minimizing a cost function on at least one of a point, a surface, and a volume within an intersection of two or more of the local field models.

33. The method of claim 30, wherein combining the local field models to generate the combined field model includes using at least one of a weighted mean of the local field models and a weighted average of the local field models, such that the local field models nearest a given location have the largest impact on the given location.

34. The method of claim 30, wherein combining the local field models to generate the combined field model includes predicting a potential at a given location using the local field models nearest the given location.

35. The method of claim 30, wherein combining the local field models to generate the combined field model includes merging the local field models into a continuous field map on a three dimensional grid of interest.

36. The method of claim 30, wherein reconciling the local field models includes determining a translation and a rotation between two or more of the local field models.

37. The method of claim 30, wherein the combined field model includes a differentiable function.

38. The method of claim 30, wherein the current injecting electrodes are mounted on one or more catheters that are secured inside the organ.

39. The method of claim 30, wherein the current injecting electrodes comprise electrodes mounted on one or more catheters secured inside the organ and one or more body-surface electrodes.

40. The method of claim 30, comprising:
processing the signals to account for respiration and heart beat by normalizing data for field variations due to the cardiac and respiratory cycles.

* * * * *